(12) United States Patent
Johnson et al.

(10) Patent No.: US 12,291,505 B2
(45) Date of Patent: May 6, 2025

(54) METHODS FOR THE SYNTHESIS OF DEUTERATED DEXTROMETHORPHAN

(71) Applicant: AVANIR PHARMACEUTICALS, INC., Aliso Viejo, CA (US)

(72) Inventors: Matt Johnson, Morrisville, NC (US); Cunxiang Zhao, Tianjin (CN); Weihua Meng, Tianjin (CN); Zhijun Lu, Tianjin (CN); Yan Li, Tianjin (CN)

(73) Assignee: AVANIR PHARMACEUTICALS, INC., Aliso Viejo, CA (US)

( * ) Notice: Subject to any disclaimer, the term of this patent is extended or adjusted under 35 U.S.C. 154(b) by 0 days.

(21) Appl. No.: 18/388,041

(22) Filed: Nov. 8, 2023

(65) Prior Publication Data

US 2024/0067608 A1 Feb. 29, 2024

Related U.S. Application Data

(62) Division of application No. 17/095,026, filed on Nov. 11, 2020, now Pat. No. 11,845,731, which is a division of application No. 16/910,353, filed on Jun. 24, 2020, now Pat. No. 10,865,187, which is a division of application No. 16/312,439, filed as application No. PCT/US2017/040623 on Jul. 3, 2017, now Pat. No. 10,730,841.

(30) Foreign Application Priority Data

Jul. 4, 2016 (WO) ................ PCT/CN2016/088414

(51) Int. Cl.
    *C07D 221/28* (2006.01)
    *C07B 59/00* (2006.01)
    *A61P 25/24* (2006.01)
    *A61P 25/28* (2006.01)

(52) U.S. Cl.
    CPC .......... *C07D 221/28* (2013.01); *C07B 59/002* (2013.01); *A61P 25/24* (2018.01); *A61P 25/28* (2018.01); *C07B 2200/05* (2013.01)

(58) Field of Classification Search
    CPC .................................................. C07D 221/28
    See application file for complete search history.

(56) References Cited

U.S. PATENT DOCUMENTS 8,710,072 B2  4/2014  Graham et al.

FOREIGN PATENT DOCUMENTS

| CN | 102977021 A | 3/2013 |
| CN | 104003936 A | 8/2014 |
| WO | WO 2007/137782 A1 | 12/2007 |
| WO | WO 2008/137474 A1 | 11/2008 |
| WO | WO 2010/062692 A1 | 6/2010 |
| WO | WO 2016/040930 A1 | 3/2016 |

OTHER PUBLICATIONS

Bolcskei et al., "Synthesis of deuterated dextromethorphan derivatives," Arkivoc: Free Online Journal of Organic Chemistry, pp. 182-193, Mar. 1, 2008.

International Search Report and Written Opinion for PCT/US2017/040623, dated Sep. 1, 2017 (12 pages).

Senderoff, "A Novel Synthesis of [O-methyl-14C]Dextromethorphan: Utility of the Vinyloxycarbonyl Group," *J. Labelled Cpd. Radiopharm.*, 2000, 43, 1283-1288.

Extended European Search Report for European Patent Application No. 24151458, dated Apr. 8, 2024 (8 pages).

*Primary Examiner* — David K O'Dell
(74) *Attorney, Agent, or Firm* — FINNEGAN, HENDERSON, FARABOW, GARRETT & DUNNER, LLP

(57) ABSTRACT

The application describes methods for making a deuterated dextromethorphan of Formula (I), deuterated dextromethorphan produced by these methods, and pharmaceutically acceptable salts thereof.

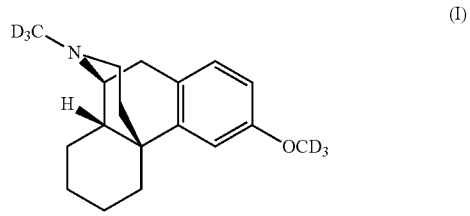

6 Claims, No Drawings

METHODS FOR THE SYNTHESIS OF DEUTERATED DEXTROMETHORPHAN

PRIORITY

This application is a divisional of U.S. patent application Ser. No. 17/095,026, filed on Nov. 11, 2020, which is a divisional of U.S. patent application Ser. No. 16/910,353, filed on Jun. 24, 2020, now U.S. Pat. No. 10,865,187, which is a divisional of U.S. patent application Ser. No. 16/312,439, filed on Dec. 21, 2018, now U.S. Pat. No. 10,730,841, which is a national stage filing under 35 U.S.C. § 371 of International Application No. PCT/US2017/040623, filed on Jul. 3, 2017, which claims the benefit of International Application No. PCT/CN2016/088414, filed on Jul. 4, 2016, which is. The contents of each of these applications are incorporated herein by reference.

FIELD

This disclosure provides methods of making deuterated dextromethorphan compounds and their pharmaceutically acceptable salts, solvates, and hydrates thereof. This disclosure also relates to deuterated dextromethorphan compounds and their pharmaceutically acceptable salts, solvates, and hydrates thereof. This disclosure also provides compositions comprising a compound of this disclosure and the use of such compositions in methods of treating diseases and conditions that are beneficially treated by administering dextromethorphan.

BACKGROUND

Dextromethorphan is currently one of the most widely used antitussives. Also known by the chemical name (+)-3-methoxy-17-methyl-(9α,13α,14α)-morphinan, dextromethorphan in the form of a product comprising dextromethorphan hydrobromide and quinidine sulfate, was approved by the U.S. Food and Drug Administration in October 2010 for the treatment of pseudobulbar affect under the tradename Nuedexta™. See www.accessdata.fda.gov/scripts/cder/ob/docs/obdetail.cfm?Appl_No=021879&TABLE1=OB_Rx Dextromethorphan (DM), the non-opioid d-isomer of the codeine analog levorphanol, has been extensively used for about 50 years as an over-the-counter (OTC) antitussive agent. DM has a complex pharmacology, with binding affinity to a number of different receptors, with primary activity in the central nervous system (CNS). DM is well known for its activity as a weak uncompetitive N-methyl-D-aspartate (NMDA) receptor antagonist ($K_i$=1500 nM) (Tortella et al. Trends Pharmacol Sci. 1989; 10(12):501-7; Chou Y C et al., Brain Res. 1999; 821(2):516-9; Netzer R et al., Eur J Pharmacol. 1993; 238(2-3):209-16; Jaffe D B et al., Neurosci Lett. 1989; 105(1-2):227-32) with the associated potential for anti-glutamate excitatory activity. DM is also a potent sigma-1 agonist (Zhou G Z et al., Eur J Pharmacol. 1991, 206(4):261-9, Maurice T et al., Brain Res Brain Res Rev. 2001, 37(1-3):116-32; Cobos E J et al., Curr Neuropharmacol. 2008; 6(4):344-66) ($K_i$=200 nM), and binds with high affinity to the serotonin transporter (SERT; $K_i$=40 nM). Although DM has only a moderate affinity for the norepinephrine transporter ($K_i$=13 µM), it effectively inhibits uptake of norepinephrine ($K_i$=240 nM) (Codd E E et al., J Pharmacol Exp Ther. 1995, 274(3):1263-70). DM is an antagonist of α3β4 nicotinic acetylcholine receptors, with a reported IC50 (concentration resulting in 50% inhibition) value of 0.7 µM (Damaj et al., J Pharmacol Exp Ther. 2005, 312(2):780-5).

As a result of one or more of these interactions, DM decreases potassium-stimulated glutamate release (Annels S J et al., Brain res. 1991, 564(2):341-3), and modulates monoamine (serotonin, norepinephrine, and dopamine) neurotransmission (Codd E E et al., J Pharmacol Exp Ther. 1995; 274(3):1263-70; Maurice T et al., Pharmacol Ther. 2009; 124(2):195-206; Maurice T et al., Prog Neuropsychopharmacol Biol Psychiatry. 1997; 21(1):69-102). DM's antagonism of α3β4 nicotinic acetylcholine receptors (Damaj M I et al., J Pharmacol Exp Ther. 2005; 312(2):780-5) may have implications for certain CNS movement disorders and addiction (Silver A A et al., J Am Acad Child Adolesc Psychiatry. 2001, 40(9):1103-10). When administered alone, DM is rapidly metabolized in the liver primarily to dextrorphan (DX) resulting in exceedingly low bioavailability and thus limiting CNS exposure. Although DX interacts with some of the same receptors as DM, but with differing affinities for key receptors, it undergoes rapid glucuronide conjugation, which largely prevents it from crossing the blood-brain barrier, thus reducing CNS effects at prescribed doses (Church J et al., Eur J Pharmacol. 1985; 111(2):185-90; Franklin P H et al., Mol Pharmacol. 1992, 41(1):134-46).

Dextromethorphan is approved for use in over-the-counter cough suppressant products. It is currently in Phase I clinical trials for treating subjects with voice spasms, and in Phase II clinical studies for treating Rett Syndrome (RTT) (www.clinicaltrials.gov). Dextromethorphan is also being evaluated in Phase II/III clinical trials for the treatment of autism spectrum disorders, and in Phase I/II clinical studies for the treatment of diabetic macular edema (www.clinicaltrials.gov).

Dextromethorphan is being studied in combination with naltrexone in a Phase II clinical trial for the treatment of Gulf War Illness, and in Phase II clinical studies with other drugs (e.g., diphenhydramine, pantoprazole, famotidine) for the treatment of acute cerebrovascular accident and cerebral edema (www.clinicaltrials.gov).

In addition, a combination of dextromethorphan hydrobromide and quinidine sulfate is currently in Phase II clinical trials for the treatment of adults with autism, and in Phase IV clinical studies for the treatment of pseudobulbar affect patients with prevalent conditions such as dementia, stroke, and traumatic brain injury (www.clinicaltrials.gov). This combination is also in Phase II clinical trials for the treatment of patients with amyotrophic lateral sclerosis, for treatment-resistant major depression, and for the prevention and modification of disease progression in episodic migraine, and it is currently in Phase IV clinical trials for the treatment of pseudobulbar affect in patients with Alzheimer's disease (www.clinicaltrials.gov).

Dextromethorphan is metabolized in the liver. Degradation begins with O- and N-demethylation to form primary metabolites dextrorphan and 3-methoxy-morphinan, both of which are further N- and O-demethylated, respectively, to 3-hydroxymorphinan (see below Biotransformation Pathway of Dextromethorphan). The cytochrome P450 enzyme 2D6 (CPY2D6) is responsible for the O-demethylation reactions of dextromethorphan and 3-methoxymorphinan. The N-demethylation of dextromethorphan and dextrorphan are catalyzed by enzymes in the related CPY3A family. Conjugates of dextrorphan and 3-hydroxymorphinan can be detected in human plasma and urine within hours of ingestion.

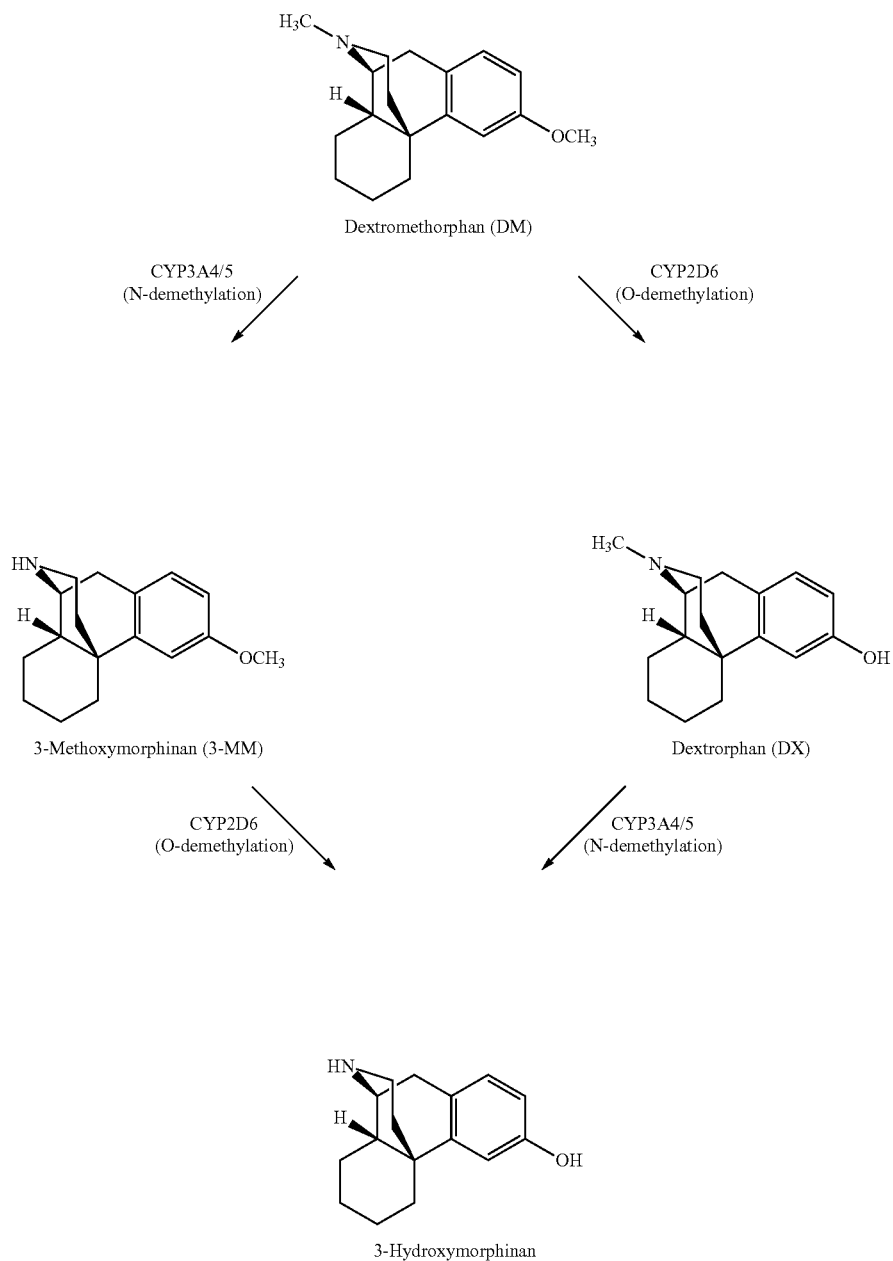

Selective incorporation of deuterium in place of hydrogen (deuteration) has the unique effect of retaining the biochemical potency and selectivity of physiologically active compounds while, in select instances, enabling substantial benefits to their overall therapeutic profile (e.g., positively impacting their metabolic rate, safety, efficacy, tolerability of a therapeutic agent). See Harbeson & Tung, *Medchem News* No. 2, May 2014; Tung, *Innovations in Pharmaceutical Technology* Issue 32, 2010. The synthesis of deuterated dextromethorphan derivatives with isotopic enrichment between 97-98% has been reported by Bölcskei et al. (Bölcskei et al., ARKIVOC, 2008: 182-193) for pharmacokinetic studies. The CD$_3$O-derivative of dextromethorphan (i.e., d3-DM) is also known, but its synthesis was not published (Bölcskei et al., ARKIVOC, 2008: 182-193, Eichold et al., J. Chromatogr B Biomed Sci Appl, 1997; 698: 147-154).

A method for synthesizing deuterated dextromethorphan is shown infra (i.e., Second Generation AVP-786 Process). This method uses three different deuterated reagents (deuterated formic acid, sodium borodeuteride, and iodomethane-D3) which complicates the supply chain, especially at commercial scale. As a result, an improved process is needed to simplify the supply chain and provide process steps which are operationally uncomplicated. Additional controls at the intermediate stages also would assure that drug substance purity is the same or better than previous processes.

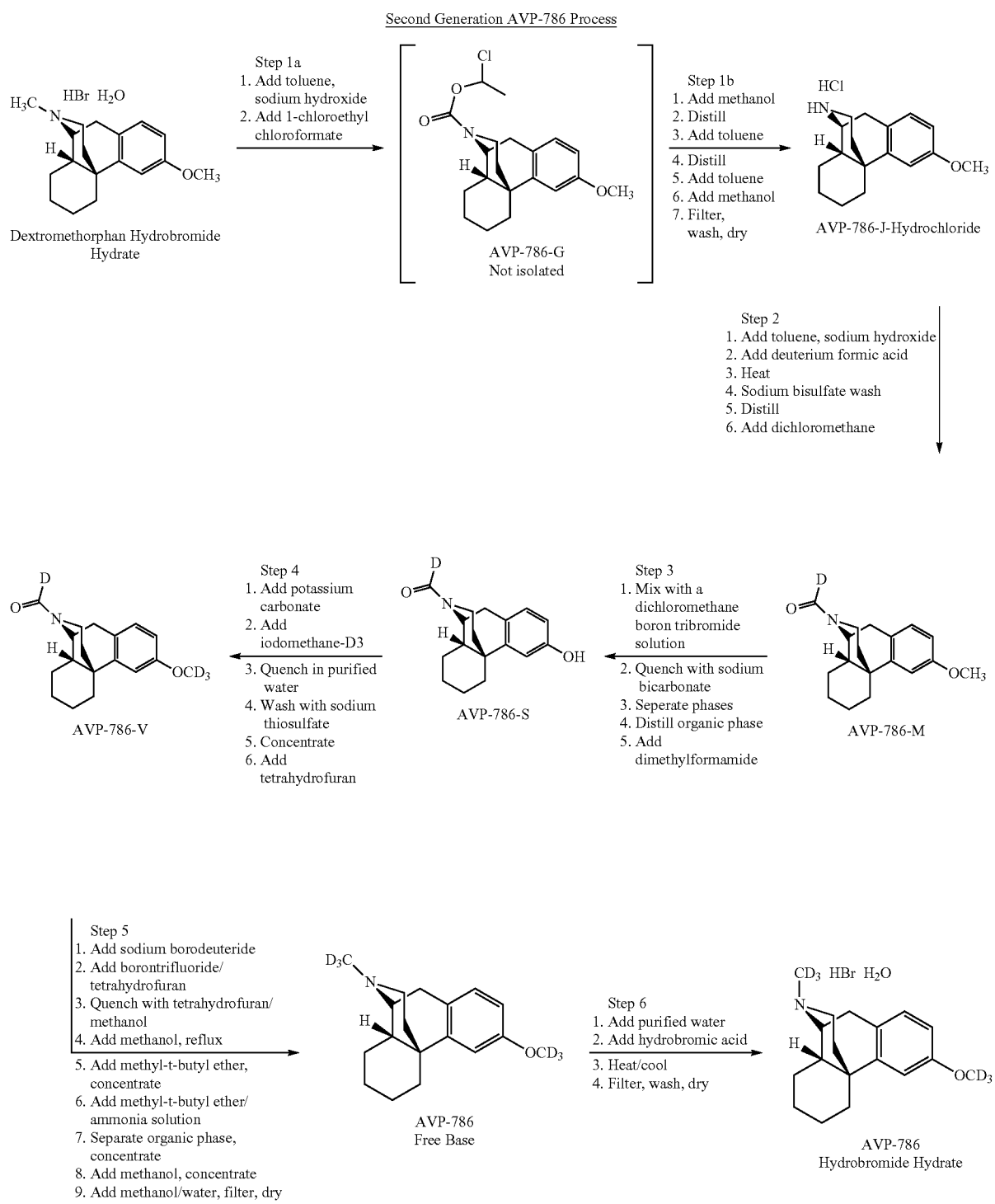

Like its undeuterated counterpart, deuterated dextromethorphan can also be metabolized in the liver. The major human metabolic pathways for d3-DM and d6-DM are shown below (Biotransformation Pathway of Deuterated Dextromethorphan). The metabolic pathway for deuterated dextromethorphan mirrors the pathway for undeuterated dextromethorphan. First, d3-DM and/or d6-DM undergo N-demethylation to form the primary metabolite d3-3-methoxymorphinan (d3-3OMM). In addition, d6-DM can also undergo O-demethylation to form the primary metabolite d3-dextrorphan (d3-DX). Then, both d3-3MM and d3-DX can be further metabolized to 3-hydroxymorphinan. The cytochrome P450 enzyme 2D6 (CPY2D6) is responsible for the O-demethylation reactions of d6-DM and d3-3MM, whereas the N-demethylation of d3- and d6-DM and d3-DX are catalyzed by enzymes in the related CPY3A family.

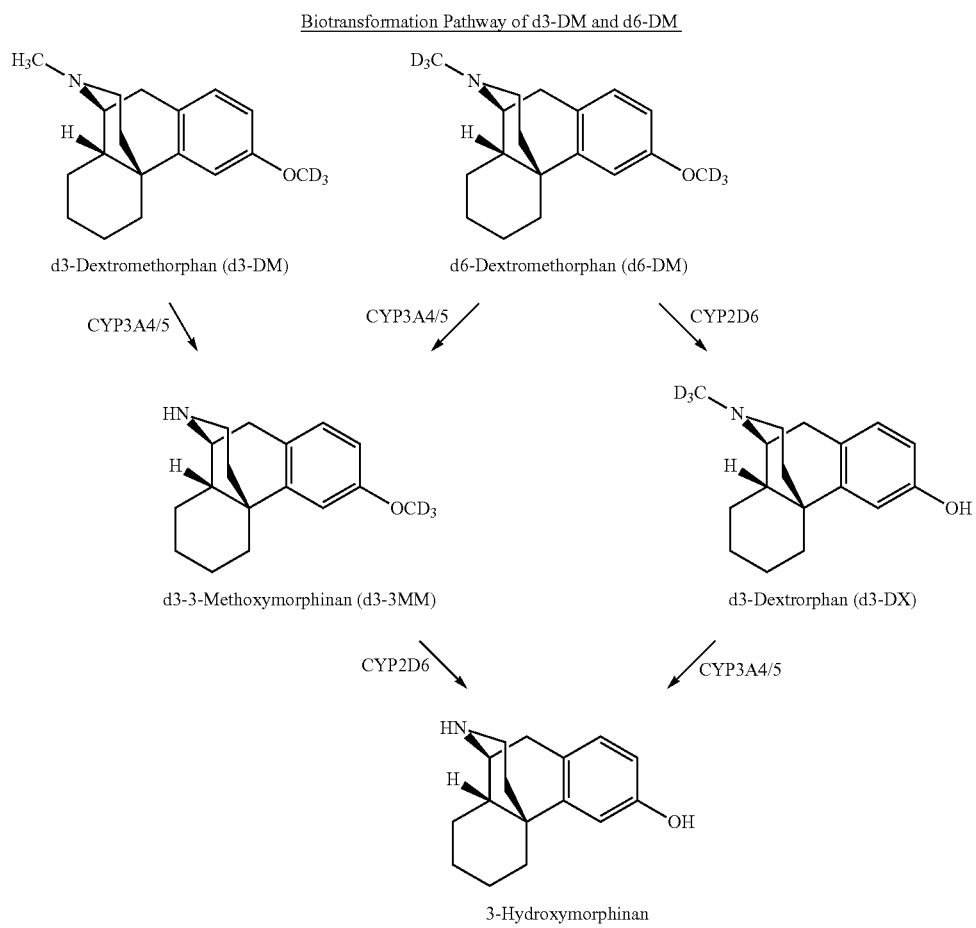

Biotransformation Pathway of d3-DM and d6-DM d3-Dextromethorphan (d3-DM)

d6-Dextromethorphan (d6-DM)

d3-3-Methoxymorphinan (d3-3MM)

d3-Dextrorphan (d3-DX)

3-Hydroxymorphinan

Dextromethorphan abuse has been linked to its active metabolite, dextrorphan. The PCP-like effects attributed to dextromethorphan are more reliably produced by dextrorphan and thus abuse-potential in humans may be attributable to dextromethorphan's metabolism to dextrorphan. See Miller, S C et al., Addict Biol, 2005, 10(4):325-7; Nicholson, K L et al., Psychopharmacology (Berl), 1999 Sep. 1, 146 (1):49-59; Pender, E S et al., Pediatr Emerg Care, 1991, 7:163-7. One study on the psychotropic effects of dextromethorphan found that extensive metabolizers reported a greater abuse potential compared to poor metabolizers, providing evidence that dextrorphan contributes to dextromethorphan abuse potential. See Zawertailo L A, et al., J Clin Psychopharmacol, 1998 August, 18(4):332-7.

A significant fraction of the population has a functional deficiency in the CYP2D6 enzyme. Thus, because the major metabolic pathway for dextromethorphan requires CYP2D6, decreased activity results in much greater duration of action and greater drug effects in CYP2D6-deficient subjects. In addition to intrinsic functional deficiency, certain medications, such as antidepressants, are potent inhibitors of the CYP2D6 enzyme. With its slower metabolism in some people, dextromethorphan, especially in combination with other medication(s), can lead to serious adverse events.

A longer than recommended duration of a drug in the body may provide continued beneficial effects, but it may also create or prolong undesired side effects. Undesirable side effects at recommended doses of dextromethorphan therapy include nausea, loss of appetite, diarrhea, drowsiness, dizziness, and impotence.

Accordingly, it is desirable to provide a compound that has the beneficial activities of dextromethorphan and may also have other benefits, e.g., reduced adverse side effects, with a decreased metabolic liability, to further extend its pharmacological effective life, enhance subject compliance, and, potentially, to decrease population pharmacokinetic variability and/or decrease its potential for dangerous drug-drug interactions or decrease the likelihood of dextromethorphan abuse due to the formation of metabolites such as dextrorphan.

SUMMARY

Convenient and economical methods for converting dextromethorphan to deuterated dextromethorphan are herein described. In one embodiment, the method provides improved isolated yields and purity for intermediates and also improved yields and purity for final compounds compared to prior methods. For example, in some embodiments, yields are >70% and purity is >90% compared to prior methods. And in some embodiments, yields are about 75% and typical purity ≥98% compared to prior methods. In one embodiment, the synthesis uses a single deuterated reagent, iodomethane-$D_3$. In some embodiments, the use of a single deuterated reagent simplifies the supply chain compared to prior methods. In one embodiment, controls at one or more intermediate stages assure that drug substance purity is the same or better than previous processes.

In one embodiment, the disclosure provides methods for synthesizing deuterated dextromethorphan compounds. In one embodiment, the disclosure provides a method for the synthesis of a deuterated dextromethorphan compound of Formula (I) or a pharmaceutically acceptable salt thereof

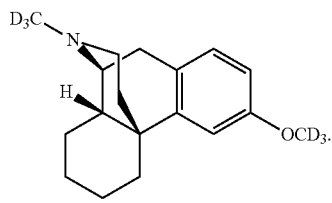
(I)

In one embodiment, the method comprises
(i) N-demethylating the tertiary amine of a dextromethorphan compound of Formula (II)

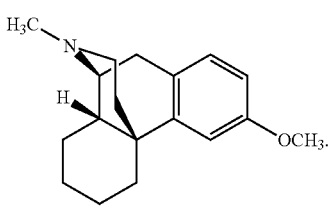
(II)

In one embodiment, the method further comprises (ii) deuterating the N-demethylated product of reaction (i) to a compound of Formula (III)

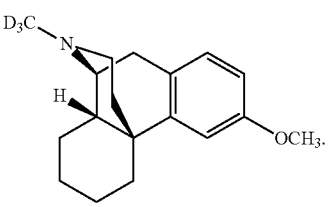
(III)

In one embodiment, the deuterating process of reaction (ii) involves N-methylation in the presence of a base and iodomethane-$D_3$. In one embodiment, the deuterating process of reaction (ii) occurs at a temperature in the range of −90° C. to 90° C. inclusive.

In one embodiment, the method further comprises, in reaction (iii), O-demethylating the methoxy group of Formula (III).

In one embodiment, the method further comprises, in reaction (iv), deuterating the O-demethylated product of reaction (iii) to the compound of Formula (I). In one embodiment, the deuterating reaction (iv) involves O-methylation in the presence of a base and iodomethane-$D_3$. In one embodiment, the deuterating reaction (iv) occurs at a temperature in the range of −10° C. to 10° C. inclusive.

In one embodiment, the N-demethylation reaction (i) is conducted in the presence of 1-chloroethyl chloroformate. In one embodiment, the N-demethylation reaction (i) further comprises adding methanol and applying heat when the N-demethylation reaction (i) is ≥93% completed. In one embodiment, the N-demethylation reaction (i) further comprises applying a vacuum when the N-demethylation is ≥98% completed until the amount of methanol is reduced to not more than 100 ppm. In one embodiment, the N-demethylation reaction (i) further comprises adding toluene before applying the vacuum.

In one embodiment, the compound of Formula (II) is present at not more than 2%.

In one embodiment, the base used in reaction (ii) for deuterating the N-demethylated product of reaction (i) to a compound of Formula (III) by N-methylation is chosen from sodium carbonate, cesium carbonate, potassium carbonate, sodium bicarbonate, potassium bicarbonate, sodium hydroxide, potassium hydroxide, potassium tert-butoxide, sodium hydride, n-butyllithium, lithium diisopropylamide, and a tertiary organic amine. In one embodiment, the tertiary organic amine base used in reaction (ii) is triethylamine or diisopropylethylamine. In one embodiment, the base used in reaction (ii) is n-butyllithium. In one embodiment, the temperature used in reaction (ii) is in the range of −90° C. to 0° C. inclusive. In one embodiment, the temperature used in reaction (ii) is in the range of −90° C. to −50° C. inclusive. In one embodiment, the temperature used in reaction (ii) is in the range of −90° C. to −70° C. inclusive.

In one embodiment, the O-demethylation reaction (iii) is conducted in the presence of hydrobromic acid.

In one embodiment, the base used in reaction (iv) for deuterating the O-demethylated compound of reaction (iii) to the compound of Formula (I) by O-methylation is chosen from potassium carbonate, sodium hydride, sodium methoxide, and potassium t-butoxide. In one embodiment, the base used in reaction (iv) is potassium t-butoxide. In one embodiment, the temperature used in reaction (iv) is in the range of −3° C. to −1° C. inclusive.

In one embodiment, the compound of Formula (I) is a hydrobromide salt. In one embodiment, the hydrobromide salt is a monohydrate.

In one embodiment, any atom not designated as deuterium in the compound is present at its natural isotopic abundance.

In one embodiment, the disclosure provides a method for synthesizing dextromethorphan compounds of Formula (I) comprising: (i) O-demethylating the methoxy group of a dextromethorphan compound of Formula (II) to a compound of Formula (VIII)

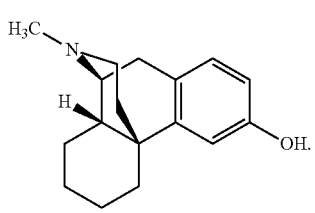
(VIII)

In one embodiment, the method further comprises (ii) deuterating the O-demethylated compound of Formula (VIII) by O-methylation to a compound of Formula (VII)

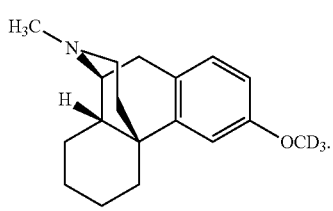

(VII)

In one embodiment, the deuterating reaction (ii) occurs in the presence of a base and iodomethane-D$_3$. In one embodiment, the deuterating reaction (ii) occurs at a temperature in the range of −10° C. to 10° C. inclusive. In one embodiment, the method further comprises (iii) N-demethylating the tertiary amine of a dextromethorphan compound of Formula (VII) from (ii) to a compound of Formula (IX)

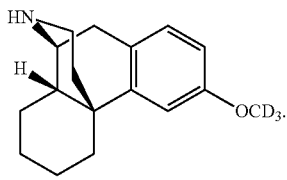

(IX)

In one embodiment, the method further comprises (iv) deuterating the N-demethylated compound of Formula (IX) to the compound of Formula (I) by N-methylation. In one embodiment, the deuterating reaction (iv) occurs in the presence of a base and iodomethane-D$_3$. In one embodiment, the deuterating reaction (iv) occurs at a temperature in the range of −90° C. to 90° C. inclusive.

In one embodiment, the O-demethylation reaction (i) is conducted in the presence of hydrobromic acid.

In one embodiment, the base used in reaction (ii) for deuterating the O-demethylated product of reaction (i) by O-methylation is chosen from potassium carbonate, sodium hydride, sodium methoxide, and potassium t-butoxide.

In one embodiment, the base used in reaction (ii) is potassium t-butoxide. In one embodiment, the temperature used in reaction (ii) is in the range of −3° C. to −1° C. inclusive.

In one embodiment, the N-demethylation reaction (iii) is conducted in the presence of 1-chloroethyl chloroformate. In one embodiment, the N-demethylation reaction described in reaction (iii) further comprises adding methanol and applying heat when the N-demethylation reaction (iii) is ≥93% completed. In one embodiment, the N-demethylation reaction (iii) further comprises applying a vacuum when the N-demethylation is ≥98% completed until the amount of methanol is reduced to not more than 100 ppm. In one embodiment, the N-demethylation reaction (iii) further comprises adding toluene before applying the vacuum. In one embodiment, the compound of Formula (VII) is present at not more than 2%.

In one embodiment, the base used in reaction (iv) for deuterating the N-demethylated compound of reaction (iii) to a compound of Formula (I) by N-methylation is chosen from sodium carbonate, cesium carbonate, potassium carbonate, sodium bicarbonate, potassium bicarbonate, sodium hydroxide, potassium hydroxide, potassium tert-butoxide, sodium hydride, n-butyllithium, lithium diisopropylamide, and a tertiary organic amine. In one embodiment, the tertiary organic amine base used in reaction (iv) is triethylamine or diisopropylethylamine. In one embodiment, the base used in reaction (iv) is n-butyllithium. In one embodiment, the temperature used in reaction (iv) is in the range of −90° C. to 0° C. inclusive. In one embodiment, the temperature used in reaction (iv) is in the range of −90° C. to −50° C. inclusive. In one embodiment, the temperature used in reaction (iv) is in the range of −90° C. to −70° C. inclusive.

In one embodiment, there is provided a method for the synthesis of a deuterated dextromethorphan compound of Formula (IV) which comprises converting the compound of Formula (I) produced by any of the methods provided herein to a hydrobromide monohydrate salt of Formula (IV) by crystallization using a solution comprising hydrobromic acid.

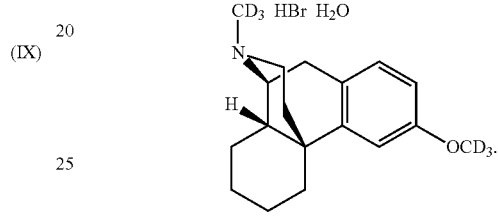

(IV)

In one embodiment, the compound of Formula (IV) is a hydrobromide salt. In one embodiment, the hydrobromide salt of a compound of Formula (IV) is a monohydrate.

In one embodiment, the methods advantageously provide ways to make deuterated dextromethorphan in significant yield by a less costly and more straightforward methodology compared to prior methods. In one embodiment, the yield of deuterated dextromethorphan is improved compared to previously-disclosed methods. In one embodiment, the methods advantageously use a single deuterated reagent, iodomethane-D$_3$, which simplifies the supply chain. In one embodiment, the single deuterated reagent is, but is not limited to, deuterated dimethyl sulfoxide, bromethane-D$_3$ (methyl-d$_3$ bromide), methyl-D$_3$ triflate, or deuterated dimethyl sulfate. A person of ordinary skill in the art would also recognize other deuterated reagents of standard methylating agents that can be used.

DETAILED DESCRIPTION

It should be understood that both the foregoing general description and the following detailed description are exemplary and explanatory but are not restrictive of the invention as claimed. Certain details of one or more embodiments of the invention are set forth in the description below. Those of skill in the art will recognize that there are numerous variations and modifications of the invention that are encompassed by its scope. Other features or advantages of the present disclosure will be apparent from the representative examples that follow, and also from the appending claims.

As used herein, nomenclature for compounds including organic compounds, can be given using common names, IUPAC, IUBMB, or CAS recommendations for nomenclature. One of skill in the art can readily ascertain the structure of a compound if given a name, either by systemic reduction of compound structure using naming conventions, or by commercially available software, such as CHEMDRAW™ (Cam bridgesoft Corporation, U.S.A.).

This disclosure includes several numeric values. It will be understood that each value disclosed herein is also herein disclosed as "about" that particular value in addition to the value itself. For example, if the value "10" is disclosed, then "about 10" is also disclosed. It is also understood that each unit between two particular units in a disclosed range are also disclosed. For example, if a range of 10-15 is disclosed, then at least 11, 12, 13, and 14 are also disclosed.

The chemistry of dextromethorphan and its analogs is described in various references such as Rodd, E. H., Ed., *Chemistry of Carbon Compounds* (Elsevier Publ., N.Y., 1960), Goodman and Gilman's Pharmacological Basis of Therapeutics, Choi *Brain Res.* 1987, 403: 333-336, and U.S. Pat. No. 4,806,543 to Choi. Its chemical structure is as follows:

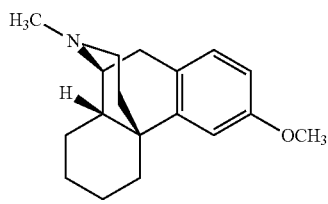

Dextromethorphan (DM) is the common name for (+)-3-methoxy-N-methylmorphinan. It is one particular molecule from a class of molecules that are dextrorotatory analogs of morphine-like opioids. The term "opiate" refers to drugs that are derived from opium, such as morphine and codeine. As used herein, the term "opioid" is broader. It includes opiates, but it also includes other drugs, natural or synthetic, which act as analgesics or sedatives in mammals.

It will be recognized that some variation of natural isotopic abundance occurs in a synthesized compound depending upon the origin of chemical materials used in the synthesis. Thus, a preparation of dextromethorphan will inherently contain small amounts of deuterated and/or $^{13}$C-containing isotopologues. The concentration of naturally abundant stable hydrogen and carbon isotopes, notwithstanding this variation, is small compared to the degree of stable isotopic substitution of compounds of this disclosure. See, e.g., Wada E et al., Seikagaku 1994, 66:15; Ganes L Z et al, Comp Biochem Physiol A Mol Integr Physiol 1998, 119:725. In a compound of this disclosure, when a particular position is designated as having deuterium, it is understood that the abundance of deuterium at that position is substantially greater than the natural abundance of deuterium, which is approximately 0.015%. In one embodiment, a position designated as having deuterium has a minimum isotopic enrichment factor of at least 3000 (45% deuterium incorporation) at each atom designated as deuterium in said compound.

As used herein, the term "isotopic enrichment factor" means the ratio between the isotopic abundance and the natural abundance of a specified isotope. In other embodiments, a compound of this disclosure has an isotopic enrichment factor for each designated deuterium atom of, but not limited to, at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this disclosure any atom not specifically designated as a particular isotope is meant to represent any stable isotope of that atom. Unless otherwise stated, when a position is designated specifically as "H" or "hydrogen," the position is understood to have hydrogen at its natural abundance isotopic composition.

As used herein, the term "isotopologue" refers to a species that has the same chemical structure and formula as a specific compound of this disclosure, with the exception of the isotopic composition at one or more positions, e.g., H vs. D. Thus an isotopologue differs from a specific compound of this disclosure in the isotopic composition thereof.

The term "compound," as used herein, is also intended to include any salts, solvates, or hydrates thereof.

As used herein, a salt of a compound of this disclosure is formed between an acid and a basic group of the compound, such as an amino functional group, or a base and an acidic group of the compound, such as a carboxyl functional group. According to another embodiment, the compound is a pharmaceutically acceptable acid addition salt.

As used herein, the term "pharmaceutically acceptable" refers to a component that is, within the scope of sound medical judgment, suitable for use in contact with the tissues of humans and other mammals without undue toxicity, irritation, allergic response, and the like, and are commensurate with a reasonable benefit/risk ratio. A "pharmaceutically acceptable salt" means any non-toxic salt that, upon administration to a recipient, is capable of providing, either directly or indirectly, a compound of this disclosure. A "pharmaceutically acceptable counterion" is an ionic portion of a salt that is not toxic when released from the salt upon administration to a recipient.

Acids commonly employed to form pharmaceutically acceptable salts include, but are not limited to, inorganic acids such as hydrogen bisulfide, hydrochloric acid, hydrobromic acid, hydroiodic acid, sulfuric acid, and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, and acetic acid, as well as related inorganic and organic acids. Such pharmaceutically acceptable salts thus include, but are not limited to, sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, hydroxybuterate, glycolate, maleate, tartrate, methanesulfonate, propanesulfonate, naphthalene-1-sulfonate, naphthalene-2-sulfonate, mandelate, and other salts.

In one embodiment, pharmaceutically acceptable acid addition salts include, but are not limited to, those formed with mineral acids such as hydrochloric acid and hydrobromic acid, and also those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present disclosure may contain an asymmetric carbon atom, for example, as the result of deuterium substitution or otherwise. As such, compounds of this disclosure can exist as either individual enantiomers, or mixtures of the two enantiomers. Accordingly, a compound of the present disclosure will include both racemic mixtures, and also individual respective stereoisomers that are substantially free from another possible stereoisomer. The term "substantially free of other stereoisomers" as used herein means less than 25% of other stereoisomers, less than 10% of other stereoisomers, less than 5% of other stereoisomers, less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting materials or intermediates.

As used herein, the term "stable compounds" refers to compounds that possess stability sufficient to allow for their manufacture and that maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

As used herein, "D" refers to deuterium.

As used herein, the terms "deuterated reagent," "deuterium reagent," and "deuterating reagent" are used interchangeably to denote a reagent in which at least one deuterium atom has been selectively incorporated in place of hydrogen (deuteration).

As used herein, "stereoisomer" refers to both enantiomers and diastereomers.

As used herein, the term "one equivalent" refers to the amount of one substance that reacts with one mole of another substance.

The present disclosure provides a compound of Formula (I), including pharmaceutically acceptable salts, solvates, and hydrates thereof.

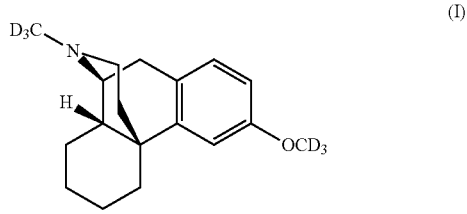

(I)

In one embodiment, the compound of Formula (I) is isolated or purified, e.g., the compound of Formula (I) is present at a purity of at least 50% by weight (e.g., at least 55%, 60%, 65%, 70%, 75%, 80%, 85%, 90%, 95%, 97%, 98%, 98.5%, 99%, 99.5% or 99.9%) of the total amount of isotopologues of Formula (I) present, respectively. Thus, in one embodiment, a composition comprising a compound of Formula (I) can include a distribution of isotopologues of the compound, provided at least 50% of the isotopologues by weight are the recited compound.

In one embodiment, any position in the compound of Formula (I) designated as having D has a minimum deuterium incorporation of at least 45% (e.g., at least 52.5%, at least 60%, at least 67.5%, at least 75%, at least 82.5%, at least 90%, at least 95%, at least 97%, at least 99%, or at least 99.5%) at the designated position(s) of the compound of Formula (I). Thus, in one embodiment, a composition comprising a compound of Formula (I) can include a distribution of isotopologues of the compound, provided at least 45% of the isotopologues include a D at the designated position(s).

In one embodiment, a compound of Formula (I) is "substantially free" of other isotopologues of the compound, e.g., less than 50%, less than 25%, less than 10%, less than 5%, less than 2%, less than 1%, or less than 0.5% of other isotopologues are present.

In one embodiment, any atom not designated as deuterium in the compound is present at its natural isotopic abundance.

In one embodiment, the method comprises (i) demethylating the tertiary amine of a dextromethorphan compound of Formula (II) or a pharmaceutically acceptable salt thereof

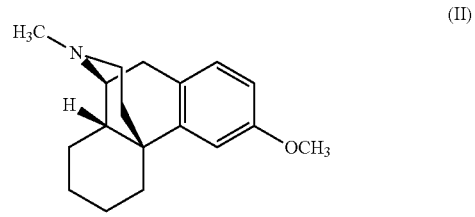 [SMILES: COc1ccc2c(c1)[C@]13CCCC[C@@H]1[C@H](C2)N(C)CC3]

(II)

to obtain a demethylated compound of Formula (V) or a pharmaceutically acceptable salt thereof

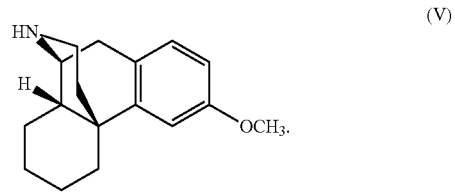 [SMILES: COc1ccc2c(c1)[C@]13CCCC[C@@H]1[C@H](C2)NCC3]

(V)

For example, in one embodiment, the N-demethylation process of a dextromethorphan compound comprises treating the dextromethorphan starting material, when present in the form of a monohydrate salt, with a base to yield the N-methylated starting material as a free base. In one embodiment, the base is an inorganic base. In one embodiment, the inorganic base can be, but is not limited to, at least one of lithium hydroxide, sodium hydroxide, potassium hydroxide, sodium bicarbonate, potassium bicarbonate, sodium carbonate, potassium carbonate, or calcium hydroxide. In one embodiment the base is sodium hydroxide. In one embodiment, a solution of dextromethorphan salt is dissolved in an organic solvent and is mixed with an aqueous basic solution and stirred. In one embodiment, the organic solvent may be, but is not limited to, toluene, hexane, chloroform, ethyl acetate, tetrahydrofuran, methylene chloride, or diethyl ether. In one embodiment, the organic solvent is toluene. In one embodiment, the organic layer is separated from the aqueous layer, and the organic layer is then washed with water to neutral pH, and azeotropically dried.

In one embodiment, the N-demethylation process is carried out with common known reagents such as cyanogen halide, acyl halide, and various chloroformates. In one embodiment, the acyl halide may be, but is not limited to, acetyl chloride. In one embodiment, the chloroformate may be, but is not limited to, at least one of 1-chloroethyl chloroformate, ethyl chloroformate, or 2,2,2-trichloroethyl chloroformate. In one embodiment, the chloroformate is 1-chloroethyl chloroformate. In one embodiment, the carbamate is subsequently removed by heating the reaction mixture and adding methanol until a compound of Formula (V) or a pharmaceutically acceptable salt thereof is obtained. In one embodiment, the N-demethylation reaction is performed at a non-extreme temperature, for example, from ambient temperature up to the reflux temperature of the reaction mixture. In one embodiment, the ambient temperature is in the range of 18° C. to 25° C. inclusive. In one embodiment, the reaction is progressed to a more elevated temperature, for example, from 30° C. to 100° C. inclusive. In one embodiment, the temperature range is 40° C. to 90° C. inclusive. In one embodiment, the temperature range is 50° C. to 80° C. inclusive. In one embodiment, the temperature range is 60° C. to 70° C. inclusive.

In one embodiment, the N-demethylation reaction may be performed under an inert atmosphere, for example but not limited to, nitrogen, to maintain a moisture-free environment. In one embodiment, the solvent may be removed to yield the intermediate carbamate. In one embodiment, the carbamate is then hydrolyzed, for example, by reaction with Zn and acetic acid in an aqueous solution, or by adding methanol and heating the reaction mixture to reflux.

In one embodiment, the N-demethylation reaction (i) is conducted in the presence of 1-chloroethyl chloroformate until the reaction is ≥93% completed. In one embodiment, the carbamate functionality is then removed using methanol and heat. In one embodiment, the methanol is removed via vacuum when the N-demethylation is ≥98% completed. In one embodiment, the amount of methanol remaining is not more than 100 ppm.

In one embodiment, an organic solvent is again added to the reaction mixture in reaction (i) and the solvent is removed under vacuum. In one embodiment, the organic solvent is, but is not limited to, toluene. In one embodiment, this procedure is repeated until the amount of methanol is about 100 ppm or less.

In one embodiment, an alcohol is added to the reaction mixture in reaction (i) to reduce impurities to target levels. In one embodiment, the alcohol is, but is not limited to, isopropanol.

In one embodiment, the impurity level for dextromethorphan is reduced to no more than 2.0%. In one embodiment, the impurity level for dextromethorphan is reduced to no more than 2.5%. In one embodiment, the impurity level for dextromethorphan is reduced to no more than 3%. In one embodiment, the impurity level for dextromethorphan is reduced to no more than 3.5%. In one embodiment, the impurity level for dextromethorphan is reduced to no more than 4%. In one embodiment, the impurity level for dextromethorphan is reduced to no more than 4.5%. In one embodiment, the impurity level for dextromethorphan is reduced to no more than 5%. In one embodiment, the impurity level for dextromethorphan is reduced to no more than 5.5%. In one embodiment, the impurity level for dextromethorphan is reduced to no more than 6%. In one embodiment, the impurity level for dextromethorphan is reduced to no more than 6.5%. In one embodiment, the impurity level for dextromethorphan is reduced to no more than 7%. In one embodiment, additional isopropanol is added in reaction (i) to reduce impurities to target levels.

In one embodiment, the compound of Formula (V) or a pharmaceutically acceptable salt thereof is isolated by filtration and rinsed with an organic solvent. In one embodiment, the organic solvent is, but is not limited to, toluene. In one embodiment, the compound of Formula (V) or a pharmaceutically acceptable salt thereof is then dried at about 50° C. until the level of organic solvent is ≤3%. In one embodiment, the compound of Formula (V) or a pharmaceutically acceptable salt thereof is dried at about 40° C. until the level of organic solvent is ≤3%. In one embodiment, the compound of Formula (V) or a pharmaceutically acceptable salt thereof is dried at about 30° C. until the level of organic solvent is ≤3%.

In one embodiment, the compound of Formula (V) or a pharmaceutically acceptable salt thereof is dried at about 40° C. until the level of organic solvent is ≤2%. In one embodiment, the compound of Formula (V) or a pharmaceutically acceptable salt thereof is dried at about 30° C. until the level of organic solvent is ≤2%.

In one embodiment, the compound of Formula (V) or a pharmaceutically acceptable salt thereof is dried at about 40° C. until the level of organic solvent is ≤1%. In one embodiment, the compound of Formula (V) or a pharmaceutically acceptable salt thereof is dried at about 30° C. until the level of organic solvent is ≤1%.

In one embodiment, the yield for the product in reaction (i) is >70% with a purity of about >90%.

In one embodiment, the method further comprises in reaction (ii) deuterating the N-demethylated compound of Formula (V) or a pharmaceutically acceptable salt thereof from reaction (i) to a compound of Formula (III)

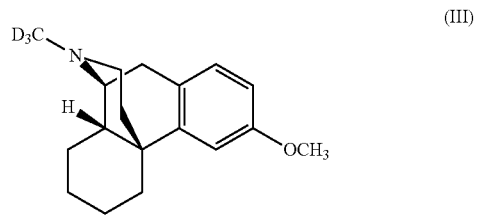 [SMILES: [2H]C([2H])([2H])N1CC[C@@]23CCCC[C@@H]2[C@@H]1Cc1ccc(OC)cc13]

by N-methylation in the presence of a base and a deuterated reagent at a temperature in the range of −90° C. to 90° C. inclusive.

In one embodiment, the N-methylation reaction may be performed under an inert atmosphere, for example nitrogen or argon, to maintain a moisture-free environment.

In one embodiment, the temperature used in reaction (ii) is in the range of −80° C. to 80° C. inclusive, −70° C. to 70° C. inclusive, −60° C. to 60° C. inclusive, −50° C. to 50° C. inclusive, −40° C. to 40° C. inclusive, −30° C. to 30° C. inclusive, −20° C. to 20° C. inclusive, or −10° C. to 10° C. inclusive.

For example, in one embodiment, reaction (ii) comprises dissolving a compound of Formula (V) or a pharmaceutically acceptable salt thereof in an organic solvent and cooling the solution. In one embodiment, the organic solvent is, but is not limited to, at least one of ethers (e.g., diethyl ether, dibutyl ether, methyl tert-butyl ether), methylene chloride, dioxane, toluene, pentane, or tetrahydrofuran. In one embodiment, the organic solvent is tetrahydrofuran. In one embodiment, the temperature is lowered to a temperature in the range of −90° C. to 0° C. inclusive. In one embodiment, the temperature is lowered to a temperature in the range of −85° C. to −5° C. inclusive, −75° C. to −15° C. inclusive, −65° C. to −25° C. inclusive, −55° C. to −35° C. inclusive, or −45° C. to −40° C. inclusive.

In one embodiment, a base is then added to reaction (ii), followed by the addition of a deuterated reagent.

In one embodiment, the deuterated reagent can be, but is not limited to, iodomethane-$D_3$, dimethyl sulfate-$D_6$, or methyl-$d_3$ triflate. In one embodiment, the deuterated reagent is iodomethane-$D_3$. In one embodiment, the reaction is carried out in a suitable base. In one embodiment, a suitable base can be, but is not limited to, an organic base (e.g., triethylamine, diisopropylethylamine) or an inorganic base (e.g., sodium carbonate, sodium hydroxide, potassium hydroxide).

In one embodiment, the bases used in reaction (ii) can be chosen from, but are not limited to, sodium carbonate, cesium carbonate, potassium carbonate, sodium bicarbonate, potassium bicarbonate, sodium hydroxide, potassium hydroxide, potassium tert-butoxide, sodium hydride, alkyllithiums (e.g., n-butyllithium, s-butyllithium, t-butyllithium, n-hexyllithium), lithium amides (e.g., lithium diisopropylamide, lithium hexamethyldesilazide), and a tertiary organic amine (e.g., trimethylamine, triethylamine, triisopropylamine, diisopropylethylamine).

In one embodiment, the tertiary organic amine is triethylamine or diisopropylethylamine. In one embodiment, the alkyllithium is n-butyllithium. In one embodiment, the lithium amide is lithium diisopropylamide.

In one embodiment, the base chosen in reaction (ii) is n-butyllithium.

In one embodiment, the base used in reaction (ii) can be used in any suitable amount or concentration that is an effective amount, i.e., that promotes or facilitates the exchange reaction (ii). For example, in one embodiment, the base is used in an amount of 0.9 to 10 equivalents. In one embodiment, the base is used in an amount of 2-8 equivalents, 3-7 equivalents, or 4-6 equivalents. In one embodiment, the base is used in an amount of 1.5 to 2.5 equivalents. In one embodiment, the base is used in an amount of 0.9 to 1.3 equivalents.

In one embodiment, the deuterated reagent used in reaction (ii) is, but is not limited to, iodomethane-$D_3$.

In one embodiment, the reaction mixture from reaction (ii) is monitored to achieve the desired conversion. In one embodiment, additional portions of deuterated reagent are added, depending on the d6-DM-J (see Scheme 1, reaction (ii)) level remaining.

In one embodiment, reaction (ii) is carried out at any suitable temperature that allows the desired N-methylation to proceed.

In one embodiment, the temperature range in reaction (ii) is −90° C. to 90° C. inclusive.

In one embodiment, the temperature used in reaction (ii) is in the range of −90° C. to 0° C. inclusive.

In one embodiment, the temperature used in reaction (ii) is in the range of −90° C. to −50° C. inclusive.

In one embodiment, the temperature used in reaction (ii) is in the range of −80° C. to −70° C. inclusive.

In one embodiment, the reaction (ii) mixture is then quenched by the addition of a quenching reagent. In one embodiment, the quenching reagent is a mildly acidic solution. In one embodiment, the quenching reagent is an organic solvent. In one embodiment, the organic solvent can be, but is not limited to, methanol or ethanol. In one embodiment, the quenching reagent is an aqueous acid. In one embodiment, the aqueous acid can be, but is not limited to, hydrochloric acid, sulfuric acid, citric acid, or acetic acid. In one embodiment, the quenching reagent is an inorganic salt. In one embodiment, the inorganic salt can be, but is not limited to, ammonium chloride, sodium bicarbonate, or a phosphate salt. In one embodiment, the quenching reagent is aqueous ammonium chloride. In one embodiment, the quenching reagent is water. In one embodiment, aqueous ammonium chloride is added to the reaction (ii) mixture and the reaction mixture is warmed under reduced pressure to remove any remaining iodomethane-D3. In one embodiment, unreacted iodomethane-D3 is evaporated under vacuum at a temperature in the range of −50° C. to −40° C. inclusive. In one embodiment, purified water is added to the reaction (ii) mixture. In one embodiment, the organic phase is then separated. In one embodiment, the aqueous phase is extracted with an organic solvent. In one embodiment, the organic solvent can be, but is not limited to, diethyl ether, or methyl-t-butyl ether. In one embodiment, the organic solvent is methyl-t-butyl ether. In one embodiment, the combined organic phase is concentrated under vacuum and the solvent is exchanged to a suitable alcohol. In one embodiment, the alcohol is, but is not limited to, at least one of methanol, ethanol, or isopropanol. In one embodiment, the alcohol is methanol. In one embodiment, purified water is slowly added and the mixture is cooled. In one embodiment, the compound of Formula (III) is isolated by filtration, washed with purified water, and dried.

In one embodiment, when the reaction is complete for the reaction (ii) mixture, additional n-butyllithium is added to consume excess iodomethane-D3. In one embodiment, the reaction (ii) mixture is then quenched by the addition of a quenching reagent. In one embodiment, the quenching reagent is a mildly acidic solution. In one embodiment, the quenching reagent is an organic solvent. In one embodiment, the organic solvent can be, but is not limited to, methanol or ethanol. In one embodiment, the quenching reagent is an aqueous acid. In one embodiment, the aqueous acid can be, but is not limited to, hydrochloric acid, sulfuric acid, citric acid, or acetic acid. In one embodiment, the quenching reagent is an inorganic salt. In one embodiment, the inorganic salt can be, but is not limited to, ammonium chloride, sodium bicarbonate, or a phosphate salt. In one embodiment, the quenching reagent is aqueous ammonium chloride. In one embodiment, purified water is then added to the reaction (ii) mixture. In one embodiment, the organic phase is then separated. In one embodiment, the aqueous phase is extracted with an organic solvent. In one embodiment, the organic solvent can be, but is not limited to, diethyl ether, or methyl-t-butyl ether. In one embodiment, the organic solvent is methyl-t-butyl ether. In one embodiment, the combined organic phase is concentrated under vacuum and the solvent is exchanged to a suitable alcohol. In one embodiment, the alcohol is, but is not limited to, at least one of methanol, ethanol, or isopropanol. In one embodiment, the alcohol is methanol. In one embodiment, purified water is slowly added and the mixture is cooled. In one embodiment, the compound of Formula (III) is isolated by filtration, washed with purified water, and dried.

In one embodiment, the compound of Formula (III) is recrystallized from methanol/water. In one embodiment, the yield is >70% with a purity >90%.

In one embodiment, the compound of Formula (III) is a hydrobromide salt.

In one embodiment, the hydrobromide salt of the compound of Formula (III) is a monohydrate.

In one embodiment, the method further comprises, in reaction (iii), the O-demethylation of the O-methylated compound of Formula (III) from reaction (ii) to a compound of Formula (VI).

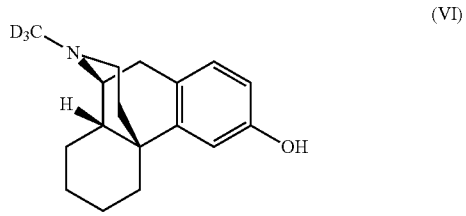 [SMILES: [2H]C([2H])([2H])N1CC[C@@]23CCCC[C@@H]2[C@@H]1Cc1ccc(O)cc13]

(VI)

For example, in one embodiment, a compound of Formula (III) is mixed with a suitable acid and heated until the d6-DM-J level is ≤1%. In one embodiment, a compound of Formula (III) is mixed with a suitable acid and heated until the d6-DM-J level is ≤1.5%. In one embodiment, a compound of Formula (III) is mixed with a suitable acid and heated until the d6-DM-J level is ≤2%. In one embodiment, a compound of Formula (III) is mixed with a suitable acid and heated until the d6-DM-J level is ≤2.5%. In one embodiment, a compound of Formula (III) is mixed with a suitable acid and heated until the d6-DM-J level is ≤3%. In one embodiment, a compound of Formula (III) is mixed with a suitable acid and heated until the d6-DM-J level is ≤3.5%. In one embodiment, a compound of Formula (III) is mixed with a suitable acid and heated until the d6-DM-J level is ≤4%. In one embodiment, a compound of Formula (III) is mixed with a suitable acid and heated until the d6-DM-J level is ≤4.5%. In one embodiment, a compound of Formula (III) is mixed with a suitable acid and heated until the d6-DM-J level is ≤5%.

In one embodiment, the acid is, but is not limited to, boron tribromide, or hydrobromic acid. In one embodiment the acid is hydrobromic acid.

In one embodiment, the reaction (iii) mixture is then cooled and mixed with a suitable base. In one embodiment, the base is, but is not limited to, at least one of sodium hydroxide, potassium hydroxide, sodium bicarbonate, potassium bicarbonate, sodium carbonate, potassium carbonate, calcium hydroxide, disodium carbonate, or ammonium hydroxide. In one embodiment, the base is potassium carbonate. In one embodiment, an organic solvent is then added to the reaction mixture. In one embodiment, the organic solvent is, but is not limited to, at least one of methylene chloride, ethyl acetate, diethyl ether, tetrahydrofuran, or 2-methyltetrahydrofuran. In one embodiment, the organic solvent is 2-methyltetrahydrofuran. In one embodiment, the organic phase is then separated and washed with purified water. In one embodiment, the combined aqueous phase is further extracted with an organic solvent. In one embodiment, the organic solvent is, but is not limited to, at least one of methylene chloride, ethyl acetate, diethyl ether, tetrahydrofuran, or 2-methyltetrahydrofuran. In one embodiment, the organic solvent is 2-methyltetrahydrofuran. In one embodiment, the combined organic phase is then concentrated under vacuum and the solvent is exchanged to a non-polar organic solvent. In one embodiment, the non-polar organic solvent is, but is not limited to, at least one of pentane, hexane, n-heptane, toluene, 1,4-dioxane, or diethyl ether. In one embodiment, the non-polar organic solvent is n-heptane. In one embodiment, the mixture is cooled, filtered, washed with the non-polar organic solvent, and dried.

In one embodiment, the yield for a compound of Formula (VI) is >70% with a purity of >96%.

In one embodiment, the method further comprises, in reaction (iv), the O-methylation of the O-demethylated compound of Formula (VI) from reaction (iii) to the compound of Formula (I) in the presence of a base and a deuterated reagent at temperatures in the range of −10° C. to 10° C. inclusive.

For example, in one embodiment, a compound of Formula (VI) is mixed with an organic solvent and the resulting solution tested for water content. In one embodiment the organic solvent can be, but is not limited to, an aprotic solvent (e.g. dioxane, diethyl ether, methylene chloride). In one embodiment, the organic solvent is, but is not limited to, at least one of methylene chloride, dioxane, tetrahydrofuran, acetonitrile, dimethyl sulfoxide, diethyl ether, or dimethylformamide. In one embodiment, the organic solvent is dimethylformamide. In one embodiment, if the water content is >0.05%, then a drying agent is added to the mixture and removed by filtration after stirring. In one embodiment, the drying agent is, but is not limited to, molecular sieves with different pore sizes. In one embodiment, the molecular sieves have a pore size from 3 Å to 5 Å. In one embodiment, the drying agent is a molecular sieve powder with a pore size of 4 Å.

In one embodiment, the O-methylation is performed in the presence of a base and iodomethane-$D_3$ at temperatures in the range of −10 to 10° C. inclusive. In one embodiment, the base can be, but is not limited to, at least one of cesium hydroxide, sodium hydroxide, potassium hydroxide, sodium carbonate, potassium carbonate, sodium hydride, sodium methoxide, sodium t-butoxide, or potassium t-butoxide.

In one embodiment, the O-methylation is performed in the presence of a base and iodomethane-$D_3$ at temperatures in the range of −3 to −1° C. inclusive.

In one embodiment, in reaction (iv) a base can be chosen from potassium carbonate, sodium hydride, sodium methoxide, and potassium t-butoxide.

In one embodiment, the base chosen in reaction (iv) is potassium t-butoxide.

In one embodiment, the O-methylation is performed in the presence of potassium t-butoxide. In one embodiment, the potassium t-butoxide is added to the reaction mixture solution and, after stirring, a solution of iodomethane-D3 in dimethylformamide is added. In one embodiment, the reaction is continued until ≤5% of a compound of Formula (VI) remains, though higher levels can be tolerated. In one embodiment, purified water is added and a compound of Formula (I) is isolated by filtration. In one embodiment, the filter cake is washed with water and dried to give a compound of Formula (I).

In one embodiment, the yield for the compound of Formula (I) is >70% with a purity of >96%.

In one embodiment, the temperature used in reaction (iv) is in the range of −10° C. to 10° C. inclusive.

In one embodiment, the temperature used in reaction (iv) is in the range of −3° C. to −1° C. inclusive.

In one embodiment, reaction (v) of the method further comprises converting the compound of Formula (I) to a pharmaceutically acceptable salt. In one embodiment, the salt is a hydrobromide monohydrate salt of Formula (IV). In one embodiment, the salt is formed by crystallization using a solution comprising of hydrobromic acid.

In one embodiment, in reaction (v), one or more solutions are filtered using a 0.45 μm filter and one or more operations are carried out in a Class 100,000 clean room. In one embodiment, purified water and a compound of Formula (I) are mixed in a reactor. In one embodiment, a hydrobromic acid solution is added, followed by purified water. In one embodiment, the resulting mixture is heated until a solution forms and then cooled to allow crystallization to occur. In one embodiment, the mixture is heated and cooled through several cycles to optimize particle size, and then cooled to ambient temperature. In one embodiment, the product is isolated by filtration, washed with purified water, and dried to give a compound of Formula (IV). In one embodiment, the drying is performed at 30-50° C. In one embodiment, the drying is performed at 40-45° C.

In one embodiment, the yield for a compound of Formula (IV) is about 75% with a purity 98%.

In one embodiment, the current disclosure also provides a method for synthesizing a deuterated dextromethorphan of Formula (I) or a pharmaceutically acceptable salt thereof comprising
(i) deuterating a dextromethorphan compound of Formula (II)

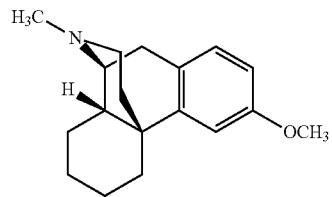

to a compound of Formula (VII)

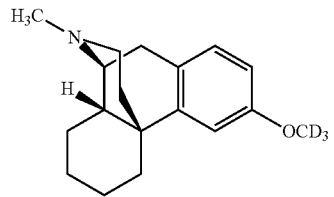

by O-demethylating the methoxy group of a dextromethorphan compound of Formula (II) to a compound of Formula (VIII)

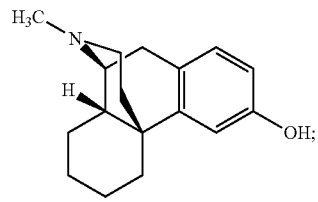

(ii) deuterating the O-demethylated reaction product of (i) to a compound of Formula (VII) by O-methylation in the presence of a base and a deuterated reagent at temperatures in the range of −10° C. to 10° C. inclusive;
(iii) N-demethylating the tertiary amine of a dextromethorphan compound of Formula (VII) to a compound of Formula (IX);

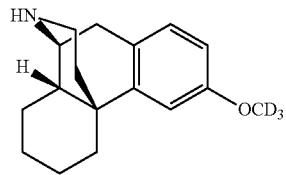

and
(iv) deuterating the N-demethylated reaction product of (iii) to the compound of Formula (I) by N-methylation in the presence of a base and a deuterated reagent at a temperature in the range of −90° C. to 90° C. inclusive.

In one embodiment, the method comprises (i) O-demethylation of the O-methylated compound of Formula (II) to a compound of Formula (VIII).

For example, in one embodiment, a compound of Formula (II) is mixed with a suitable acid and heated until the starting material (i.e., a compound of Formula II) level is ≤1%. In one embodiment, the acid is, but is not limited to, boron tribromide, or hydrobromic acid. In one embodiment the acid is hydrobromic acid.

In one embodiment, the reaction (i) mixture is then cooled and mixed with a suitable base. In one embodiment, the base is, but is not limited to, at least one of sodium hydroxide, potassium hydroxide, sodium bicarbonate, potassium bicarbonate, sodium carbonate, potassium carbonate, calcium hydroxide, disodium carbonate, or ammonium hydroxide. In one embodiment, the base is potassium carbonate. In one embodiment, an organic solvent is then added to the reaction mixture. In one embodiment, the organic solvent is, but is not limited to, at least one of methylene chloride, ethyl acetate, diethyl ether, tetrahydrofuran, or 2-methyltetrahydrofuran. In one embodiment, the organic solvent is 2-methyltetrahydrofuran. In one embodiment, the organic phase is then separated and washed with purified water. In one embodiment, the combined aqueous phase is further extracted with an organic solvent. In one embodiment, the organic solvent is, but is not limited to, at least one of methylene chloride, ethyl acetate, diethyl ether, tetrahydrofuran, or 2-methyltetrahydrofuran. In one embodiment, the organic solvent is 2-methyltetrahydrofuran. In one embodiment, the combined organic phase is then concentrated under vacuum and the solvent is exchanged with an organic solvent. In one embodiment, the organic solvent is a non-polar organic solvent. In one embodiment, the non-polar organic solvent is, but is not limited to, at least one of pentane, hexane, n-heptane, toluene, 1,4-dioxane, or diethyl ether. In one embodiment, the non-polar organic solvent is n-heptane. In one embodiment, the mixture is cooled, filtered, washed with the non-polar organic solvent, and dried to yield a compound of Formula (VIII). In one embodiment, the yield for a compound of Formula (VIII) is >70% with a purity of >96%.

In one embodiment, the method comprises reaction (ii) O-methylation of the O-demethylated compound of Formula (VIII) from reaction (i) to the compound of Formula (VII) in the presence of a base and a deuterated reagent at temperatures in the range of −10° C. to 10° C. inclusive.

For example, in one embodiment, a compound of Formula (VIII) is mixed with an organic solvent and the resulting solution tested for water content. In one embodiment the organic solvent can be, but is not limited to, an aprotic solvent (e.g. dioxane, diethyl ether, methylene chloride). In one embodiment, the organic solvent is, but is not limited to, at least one of methylene chloride, dioxane, tetrahydrofuran, acetonitrile, dimethyl sulfoxide, diethyl ether, or dimethylformamide. In one embodiment, the organic solvent is dimethylformamide. In one embodiment, if the water content of the mixture is >0.05%, then a drying agent is added to the mixture and removed by filtration after stirring. In one embodiment, the drying agent is, but is not limited to, molecular sieves with different pore sizes. In one embodiment, the molecular sieves have a pore size from 3 Å to 5 Å. In one embodiment, the drying agent is a molecular sieve powder with a pore size of 4 Å.

In one embodiment, the O-methylation reaction is performed in the presence of a base and iodomethane-$D_3$ at temperatures in the range of –10 to 10° C. inclusive. In one embodiment, the base can be, but is not limited to, at least one of cesium hydroxide, sodium hydroxide, potassium hydroxide, sodium carbonate, potassium carbonate, sodium hydride, sodium methoxide, sodium t-butoxide, or potassium t-butoxide.

In one embodiment, the O-methylation reaction is performed in the presence of a base and a deuterated reagent at temperatures in the range of –3 to –1° C. inclusive.

In one embodiment, the deuterated reagent used in the O-methylation reaction (ii) is iodomethane-$D_3$.

In one embodiment, in reaction (ii) a base can be chosen from potassium carbonate, sodium hydride, sodium methoxide, and potassium t-butoxide.

In one embodiment, the base chosen for reaction (ii) is potassium t-butoxide.

In one embodiment, the O-methylation reaction is performed in the presence of potassium t-butoxide. In one embodiment, the potassium t-butoxide is added to the reaction mixture solution and, after stirring, a solution of iodomethane-D3 in dimethylformamide is added. In one embodiment, the reaction is continued until ≤5% of a compound of Formula (VIII) remains, though higher levels can be tolerated. In one embodiment, purified water is added and a compound of Formula (VII) is isolated by filtration. In one embodiment, the filter cake is washed with water and dried to give a compound of Formula (VII). In one embodiment, the yield for the compound of Formula (VII) is >70% with a purity of >96%.

In one embodiment, the temperature used in reaction (ii) is in the range of –10° C. to 10° C. inclusive.

In one embodiment, the temperature used in reaction (ii) is in the range of –3° C. to –1° C. inclusive.

In one embodiment, the N-demethylation reaction (iii) can be carried out with common known reagents such as, but not limited to, cyanogen halide, acyl halide, and various chloroformates. In one embodiment, the acyl halide may be, but is not limited to, acetyl chloride. In one embodiment, the chloroformate may be, but is not limited to, at least one of 1-chloroethyl chloroformate, ethyl chloroformate, or 2,2,2-trichloroethyl chloroformate. In one embodiment, the chloroformate is 1-chloroethyl chloroformate. In one embodiment, the carbamate is subsequently removed by heating the reaction mixture and adding methanol until a compound of Formula (IX) or a pharmaceutically acceptable salt thereof is obtained. In one embodiment, the N-demethylation reaction is performed at a non-extreme temperature, for example, from ambient temperature up to the reflux temperature of the reaction mixture. In one embodiment, the reaction can be progressed to a more elevated temperature, for example, from 30° C. to 100° C. inclusive. In one embodiment, the temperature range is 40° C. to 90° C. inclusive. In one embodiment, the temperature range is 50° C. to 80° C. inclusive. In one embodiment, the temperature range is 60° C. to 70° C. inclusive.

In one embodiment, the N-demethylation reaction may be performed under an inert atmosphere, for example nitrogen or argon, to maintain a moisture-free environment. In one embodiment, the solvent may be removed to yield the intermediate carbamate. This is then hydrolyzed, for example, by reaction with Zn and acetic acid in an aqueous solution, or by adding methanol and heating the reaction mixture to reflux.

In one embodiment, the N-demethylation reaction (iii) is conducted in the presence of 1-chloroethyl chloroformate until the reaction is 93% completed. In one embodiment, the carbamate functionality is then removed using methanol and heat. In one embodiment, the methanol is removed via vacuum when the N-demethylation is ≥98% completed. In one embodiment, the amount of methanol remaining is not more than 100 ppm.

In one embodiment, an organic solvent is again added to the reaction (iii) mixture and the solvent is removed under vacuum. In one embodiment, the organic solvent is, but is not limited to, toluene. In one embodiment, this procedure is repeated until the amount of methanol is about 100 ppm or less.

In one embodiment, an alcohol is added to the reaction (iii) mixture to reduce impurities to target levels. In one embodiment, the alcohol is, but is not limited to, isopropanol. In one embodiment, the level of impurity of a compound of Formula (VII) is determined by HPLC.

In one embodiment, the target level of impurity for a compound of Formula (VII) is reduced to no more than 0.5%.

In one embodiment, the impurity level for a compound of Formula (VII) is reduced to no more than 2.0%.

In one embodiment, additional isopropanol is added to the product of reaction (iii) to reduce impurities to target levels.

In one embodiment, the compound of Formula (IX) or a pharmaceutically acceptable salt thereof is isolated by filtration and rinsed with an organic solvent. In one embodiment, the organic solvent is, but is not limited to, toluene. In one embodiment, the compound of Formula (IX) or a pharmaceutically acceptable salt thereof is then dried at about 50° C. until the level of organic solvent is ≤3%. In one embodiment, the compound of Formula (IX) or a pharmaceutically acceptable salt thereof is dried at about 40° C. until the level of organic solvent is ≤3%. In one embodiment, the compound of Formula (IX) or a pharmaceutically acceptable salt thereof is dried at about 30° C. until the level of organic solvent is ≤3%.

In one embodiment, the compound of Formula (IX) or a pharmaceutically acceptable salt thereof is dried at about 40° C. until the level of organic solvent is ≤2%. In one embodiment, the compound of Formula (IX) or a pharmaceutically acceptable salt thereof is dried at about 30° C. until the level of organic solvent is ≤2%.

In one embodiment, the compound of Formula (IX) or a pharmaceutically acceptable salt thereof is dried at about 40° C. until the level of organic solvent is ≤1%. In one embodiment, the compound of Formula (IX) or a pharmaceutically acceptable salt thereof is dried at about 30° C. until the level of organic solvent is ≤1%.

In one embodiment, the yield for the product obtained in reaction (iii) is >70% with a purity of about >90%.

In one embodiment, the method comprises in reaction (iv) deuterating the N-demethylated compound of Formula (IX) or a pharmaceutically acceptable salt thereof from reaction (iii) to a compound of Formula (I) by N-methylation in the presence of a base and a deuterated reagent at a temperature in the range of −90° C. to 90° C. inclusive.

In one embodiment, the temperature used in reaction (iv) is in the range of −80° C. to 80° C. inclusive, −70° C. to 70° C. inclusive, −60° C. to 60° C. inclusive, −50° C. to 50° C. inclusive, −40° C. to 40° C. inclusive, −30° C. to 30° C. inclusive, −20° C. to 20° C. inclusive, or −10° C. to 10° C. inclusive.

For example, in one embodiment, reaction (iv) comprises dissolving a compound of Formula (IX) or a pharmaceutically acceptable salt thereof in an organic solvent and cooling the solution. In one embodiment, the organic solvent is, but is not limited to, at least one of ethers (e.g., diethyl ether, dibutyl ether, methyl tert-butyl ether), methylene chloride, dioxane, or tetrahydrofuran. In one embodiment, the organic solvent is tetrahydrofuran. In one embodiment, a low temperature is in the range of −90° C. to 0° C. inclusive. In one embodiment, a low temperature is in the range of −85° C. to −5° C. inclusive, −75° C. to −15° C. inclusive, −65° C. to −25° C. inclusive, −55° C. to −35° C. inclusive, or −45° C. to −40° C. inclusive.

In one embodiment, a base is then added in reaction (iv), followed by the addition of a deuterated reagent.

In one embodiment, the deuterated reagent can be, but is not limited to, iodomethane-$D_3$. In one embodiment, the reaction is carried out in a suitable base. In one embodiment, a suitable base can be, but is not limited to, an organic base (e.g., triethylamine, diisopropylethylamine) or an inorganic base (e.g., sodium carbonate, sodium hydroxide, potassium hydroxide).

In one embodiment, bases for reaction (iv) can be chosen from, but are not limited to, sodium carbonate, cesium carbonate, potassium carbonate, sodium bicarbonate, potassium bicarbonate, sodium hydroxide, potassium hydroxide, potassium tert-butoxide, sodium hydride, alkyllithiums (e.g., n-butyllithium, s-butyllithium, t-butyllithium, n-hexyllithium), lithium amides (e.g., lithium diisopropylamide, lithium hexamethyldesilazide), and a tertiary organic amine (e.g., trimethylamine, triethylamine, triisopropylamine, diisopropylethylamine).

In one embodiment, the tertiary organic amine used in reaction (iv) is triethylamine or diisopropylethylamine. In one embodiment, the alkyllithium base used in reaction (iv) is n-butyllithium. In one embodiment, the lithium amide base is lithium diisopropylamide.

In one embodiment, the base chosen in reaction (iv) is n-butyllithium.

In one embodiment, the base used in reaction (iv) can be used in any suitable amount or concentration that is an effective amount, i.e., that promotes or facilitates the exchange reaction in step (iv). For example, in one embodiment, the base is used in an amount of 0.9 to 10 equivalents. In one embodiment, the base is used in an amount of 2-8 equivalents, 3-7 equivalents, or 4-6 equivalents. In one embodiment, the base is used in an amount of 1.5 to 2.5 equivalents. In one embodiment, the base is used in an amount of 0.9 to 1.3 equivalents.

In one embodiment, the deuterated reagent used in reaction (iv) is iodomethane-$D_3$.

In one embodiment, the reaction (iv) mixture is monitored to achieve the desired conversion. In one embodiment, additional portions of deuterated reagent are added to consume the starting material.

In one embodiment, reaction (iv) is carried out at any suitable temperature that allows the desired N-methylation to proceed.

In one embodiment, the temperature range in step (iv) is −90° C. to 90° C. inclusive.

In one embodiment, the temperature used in reaction (iv) is in the range of −90° C. to 0° C. inclusive.

In one embodiment, the temperature used in reaction (iv) is in the range of −90° C. to −50° C. inclusive.

In one embodiment, the temperature used in reaction (iv) is in the range of −80° C. to −70° C. inclusive.

In one embodiment, in reaction (iv) the reaction mixture is then quenched by the addition of a quenching reagent. In one embodiment, the quenching reagent is a mildly acidic solution. In one embodiment, the quenching reagent is, but is not limited to, aqueous ammonium chloride. In one embodiment, in reaction (iv) aqueous ammonium chloride is added and the mixture is warmed under reduced pressure to remove any remaining iodomethane-D3. In one embodiment, unreacted iodomethane-D3 is evaporated under vacuum at a temperature in the range of −50° C. to −40° C. inclusive. In one embodiment, purified water is added to the reaction (iv) mixture. In one embodiment, the organic phase is then separated. In one embodiment, the aqueous phase is extracted with an organic solvent. In one embodiment, the organic solvent can be, but is not limited to, diethyl ether, or methyl-t-butyl ether. In one embodiment, the organic solvent is methyl-t-butyl ether. In one embodiment, the combined organic phase is concentrated under vacuum and the solvent is exchanged with a suitable alcohol. In one embodiment, the alcohol is, but is not limited to, at least one of methanol, ethanol, or isopropanol. In one embodiment, the alcohol is methanol. In one embodiment, purified water is slowly added and the mixture is cooled. In one embodiment, the compound of Formula (I) is isolated by filtration, washed with purified water, and dried.

In one embodiment, the compound of Formula (I) is recrystallized from methanol/water. In one embodiment, the yield is >70% with a purity >90%.

In one embodiment, the method comprises in reaction (v) converting the compound of Formula (I) to a pharmaceutically acceptable salt. In one embodiment, the salt is a hydrobromide monohydrate salt of Formula (IV). In one embodiment, the salt is formed by crystallization using a solution comprising of hydrobromic acid.

In one embodiment, in reaction (v), one or more solutions are filtered using a 0.45 μm filter and one or more operations are carried out in a Class 100,000 clean room. In one embodiment, purified water and a compound of Formula (I) are mixed in a reactor. In one embodiment, a hydrobromic acid solution is added, followed by purified water. In one embodiment, the resulting mixture is heated until a solution forms and then cooled to allow crystallization to occur. In one embodiment, the mixture is heated and cooled through several cycles to optimize particle size, and then cooled to ambient temperature. In one embodiment, the product is isolated by filtration, washed with purified water, and dried to give a compound of Formula (IV). In one embodiment, the drying is performed at 30-50° C. In one embodiment, the drying is performed at 40-45° C.

In one embodiment, the yield for a compound of Formula (IV) is about 75% with a purity ≥98%.

Schemes 1 and 2 show exemplary routes to deuterated dextromethorphan of Formula (I). Scheme 3 shows an exemplary route to a compound of Formula (IV). As shown in Scheme 1, dextromethorphan hydrobromide monohydrate is initially treated in reaction (i) with sodium hydroxide followed then by acylation of the amine using 1-chloroethyl chloroformate, and subsequent removal of the carbamate by heating the reaction mixture and adding methanol until d6-DM-J HCl is obtained. Then, in reaction (ii) compound d6-DM-J HCl is N-methylated, in the presence of n-BuLi, with an appropriately deuterated iodomethane to yield d6-DM-F or a compound of Formula (III). In reaction (iii) compound d6-DM-F or a compound of Formula (iii) is O-demethylated using hydrobromic acid to yield the alcohol d6-DM-H or a compound of Formula VI. Compound d6-DM-H or a compound of Formula (VI) is then treated in reaction (iv), in the presence of potassium t-butoxide, with an appropriately deuterared iodomethane to yield d6-DM Free Base or a compound of Formula (I).

As shown in Scheme 2, in reaction (i) a compound of Formula (II) is O-demethylated using hydrobromic acid to yield the alcohol of Formula (VIII). A compound of Formula (VIII) is O-methylated in reaction (ii), in the presence of potassium t-butoxide, with an appropriately deuterated iodomethane to yield a compound of Formula (VII). Then, a compound of Formula (VII) is N-acylated in reaction (iii) using 1-chloroethyl chloroformate followed by the subsequent removal of the carbamate by heating the reaction mixture and adding methanol until a compound of Formula (IX) is obtained. Then, in reaction (iv) a compound of Formula (IX) is N-methylated, in the presence of n-BuLi, with an appropriately deuterated iodomethane to yield a compound of Formula (I).

Preparation of a compound of Formula (IV) is achieved via Scheme 3 using a compound of Formula (I) which can be obtained as shown in Schemes 1 or 2. Treatment of a compound of d6-DM free base or a compound of Formula (I) with water and hydrobromic acid solution followed by repeated heating and cooling yields d6-DM hydrobromide monohydrate or a compound of Formula (IV).

An exemplary route for the synthesis of a compound of Formula (I) is shown in Scheme 1.

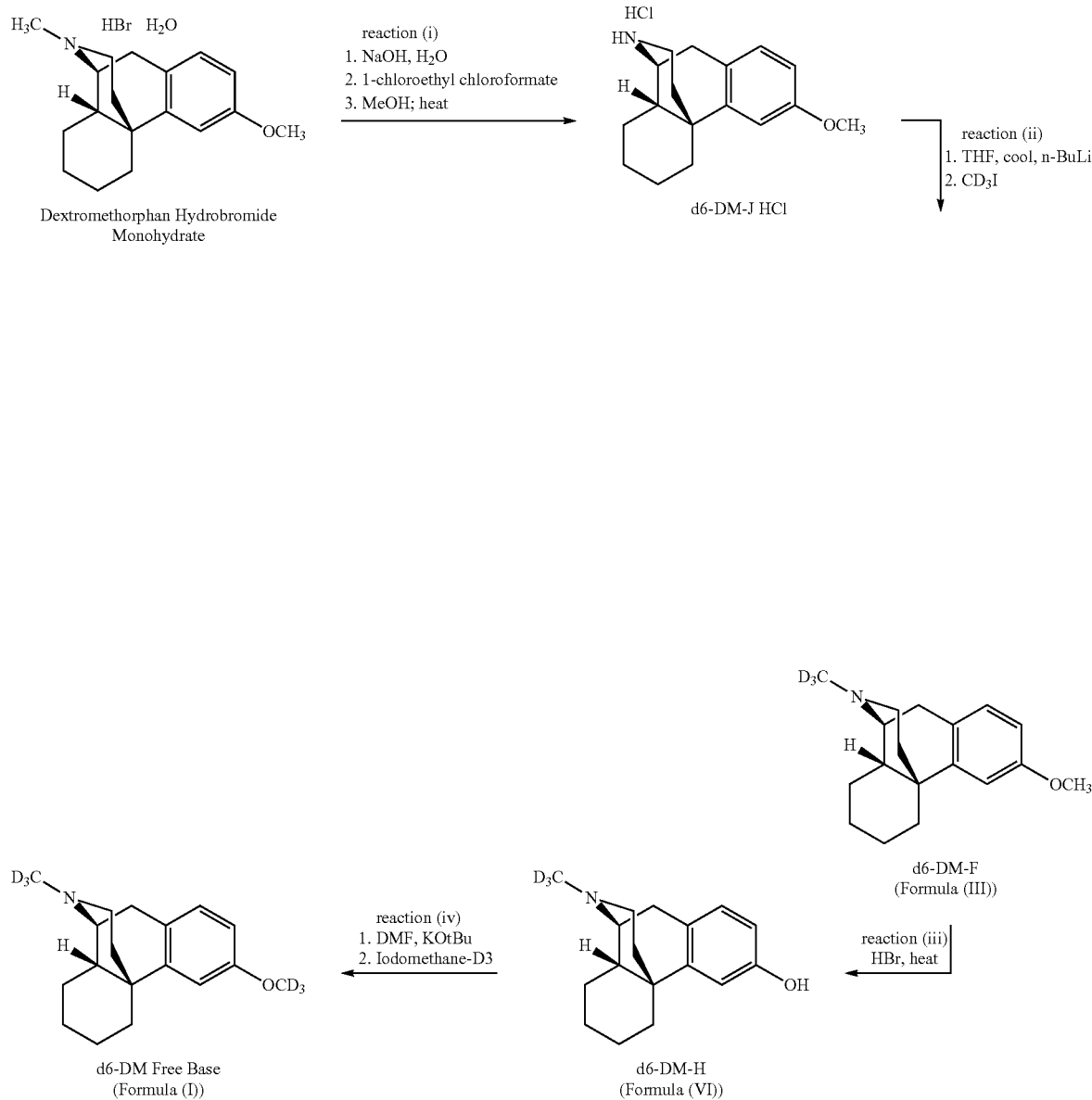

An exemplary alternative route for the synthesis of a compound of Formula (I) is shown in Scheme 2.

thetic precursors, including those within routes not explicitly shown in the schemes herein, are within the means of

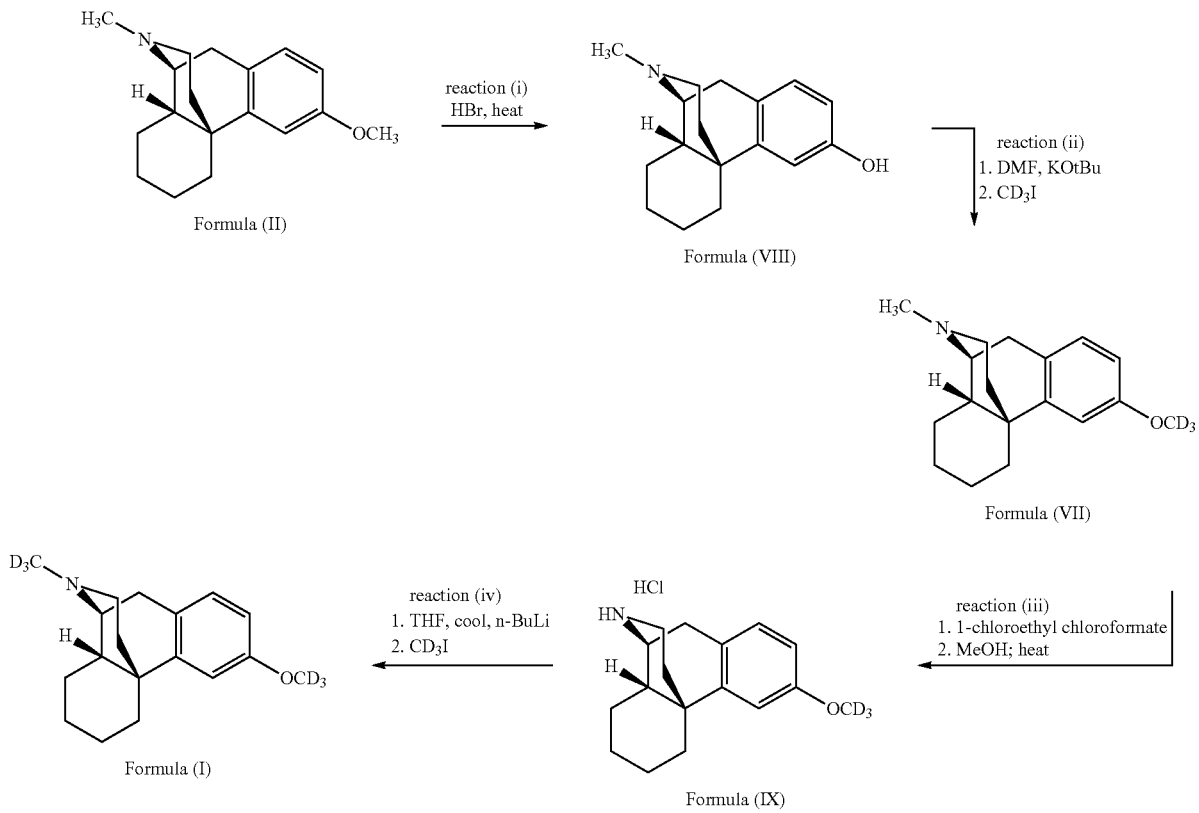

Scheme 2

An exemplary route for the synthesis of a compound of Formula (IV) is shown in Scheme 3.

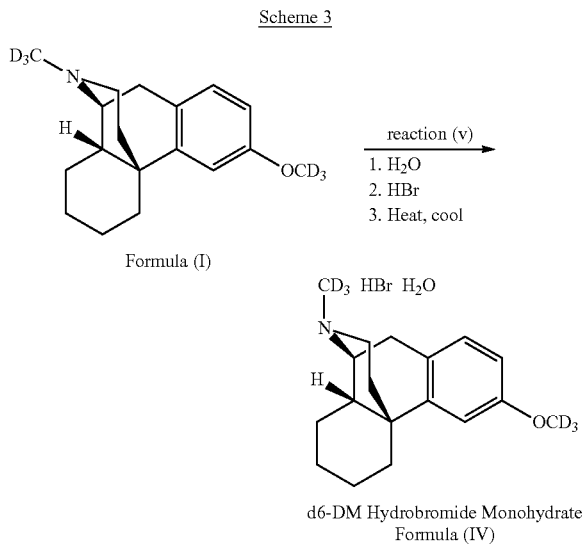

Scheme 3

The specific approaches and compounds shown above are not intended to be limiting. Additional methods of synthesizing compounds of Formulas (I) and (IV) and their synchemists of ordinary skill in the art. Synthetic chemistry transformations and protecting group methodologies (protection and deprotection) useful in synthesizing the applicable compounds are known in the art and include, for example, those described in Larock R, Comprehensive Organic Transformations, VCH Publishers (1989); Greene T W et al., Protective Groups in Organic Synthesis, 3$^{rd}$ Ed., John Wiley and Sons (1999); Fieser L et al., Fieser and Fiesre's Reagents for Organic Synthesis, John Wiley and SOns (1994); and Paquette L, ed., Encyclopedia of Reagents for Organic Synthesis, John Wiley and Sons (1995) and subsequent editions thereof.

Compositions

The disclosure also provides compositions comprising a compound of Formula I, or a pharmaceutically acceptable salt, solvate, or hydrate of said compound. In one embodiment, a composition of this disclosure is formulated for pharmaceutical use ("a pharmaceutical composition"), wherein the composition comprises a pharmaceutically acceptable carrier. The carrier(s) are "pharmaceutically acceptable" in the sense of being compatible with the other ingredients of the formulation and not deleterious to the recipient thereof in an amount used in the medicament. In one embodiment, the composition may comprise an adjuvant. In one embodiment, the composition may comprise a vehicle.

In one embodiment, pharmaceutically acceptable carriers, adjuvants, and vehicles that may be used in the pharmaceutical compositions of this disclosure include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

In one embodiment, if desired, the solubility and bioavailability of the compounds of the present disclosure in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Inter-science, 2006.

In one embodiment, another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide. See U.S. Pat. No. 7,014,866; and United States Patent Publications 2006/0094744 and 2006/0079502.

In one embodiment, the pharmaceutical compositions of the disclosure include those suitable for oral (e.g., tablets, sustained release capsules, and in liposomes), rectal, nasal, topical (including buccal and sublingual), vaginal, or parenteral (including subcutaneous, intramuscular, intravenous and intradermal) administration. In one embodiment, the compound of the formulae herein is administered transdermally (e.g., using a transdermal patch or iontophoretic techniques). Other formulations may conveniently be presented in unit dosage form, and may be prepared by any methods well known in the art of pharmacy. See, for example, Remington's Pharmaceutical Sciences, Mack Publishing Company, Philadelphia, Pa. (17th ed. 1985).

In one embodiment, such preparative methods include the step of bringing into association with the molecule to be administered ingredients such as the pharmaceutically acceptable carrier. In one embodiment, the compositions are prepared by uniformly and intimately bringing into association the active ingredients with one or more of liquid carriers, liposomes, or finely divided solid carriers, and then, if desired, shaping the product.

In one embodiment, the compound is administered orally. Compositions of the present disclosure suitable for oral administration may be presented as discrete units such as, but not limited to, capsules, sachets, or tablets each containing a predetermined amount of the active ingredient; a powder or granules; a solution or a suspension in an aqueous liquid, or a non-aqueous liquid; an oil-in-water liquid emulsion; a water-in-oil liquid emulsion; packed in liposomes; or as a bolus, etc. In one embodiment, soft gelatin capsules can be useful for containing such suspensions, which may beneficially increase the rate of compound absorption.

In the case of tablets for oral use, carriers that are commonly used include, but are not limited to, lactose and corn starch. Lubricating agents, such as, but not limited to, magnesium stearate, are also typically added. For oral administration in a capsule form, useful diluents include, but are not limited to, lactose and dried cornstarch. When aqueous suspensions are administered orally, the active ingredient is typically combined with emulsifying and suspending agents. In one embodiment, if desired, certain sweetening and/or flavoring and/or coloring agents may be added. In one embodiment, compositions suitable for oral administration include, but are not limited to, lozenges comprising the ingredients in a flavored basis, usually sucrose and acacia or tragacanth; and pastilles comprising the active ingredient in an inert basis such as gelatin and glycerin, or sucrose and acacia.

In one embodiment, compositions suitable for parenteral administration include, but are not limited to, aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. In one embodiment, the formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. In one embodiment, extemporaneous injection solutions and suspensions may be prepared from sterile powders, granules and tablets.

In one embodiment, such injection solutions may be in the form, for example, of a sterile injectable aqueous or oleaginous suspension. This suspension may be formulated according to techniques known in the art using suitable dispersing or wetting agents (such as, for example, Tween 80) and suspending agents. In one embodiment, the sterile injectable preparation may also be a sterile injectable solution or suspension in a non-toxic parenterally-acceptable diluent or solvent, for example, as a solution in 1,3-butanediol. In one embodiment, among the acceptable vehicles and solvents that may be employed are, but are not limited to, mannitol, water, Ringer's solution, and isotonic sodium chloride solution. In addition, sterile, fixed oils are conventionally employed as a solvent or suspending medium. For this purpose, any bland fixed oil may be employed including, but not limited to, synthetic mono- or diglycerides. Fatty acids, such as oleic acid and its glyceride derivatives are useful in the preparation of injectables, as are natural pharmaceutically-acceptable oils, such as, but not limited to, olive oil or castor oil, especially in their polyoxyethylated versions. In one embodiment, these oil solutions or suspensions may also contain a long-chain alcohol diluent or dispersant.

In one embodiment, the pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax, and polyethylene glycols.

In one embodiment, the pharmaceutical compositions of this disclosure may be administered by nasal aerosol or inhalation. Such compositions are prepared according to techniques well-known in the art of pharmaceutical formulation, and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

In one embodiment, topical administration of the pharmaceutical compositions of this disclosure may be used when the desired treatment involves areas or organs readily accessible by topical application. For topical application to the skin, the pharmaceutical composition may be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax, and water. In one embodiment, the pharmaceutical composition can be formulated with a suitable lotion or cream containing the active compound suspended or dissolved in a carrier. In one embodiment, suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

In one embodiment, application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers, or other device which provides for internal access.

Thus, according to one embodiment, the compounds of this disclosure may be incorporated into compositions for coating an implantable medical device, such as prostheses, artificial valves, vascular grafts, stents, or catheters. In one embodiment, suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant, or vehicle, as those terms are used herein.

In one embodiment, the disclosure provides an implantable drug release device impregnated with or containing a compound or a composition comprising a compound of this disclosure, such that said compound is released from said device and is therapeutically active. Implantable drug release devices include, but are not limited to, biodegradable polymer capsules or bullets, non-degradable, diffusible polymer capsules, and biodegradable polymer wafers.

In one embodiment, the disclosure provides an implantable medical device coated with a compound or a composition comprising a compound of this disclosure, such that said compound is therapeutically active.

Where an organ or tissue is accessible because of removal from the subject, such organ or tissue may be bathed in a medium containing a composition of this disclosure, a composition of this disclosure may be painted onto the organ, or a composition of this disclosure may be applied in any other convenient way.

In one embodiment, a composition of this disclosure further comprises a second therapeutic agent. The second therapeutic agent may be selected from any compound or therapeutic agent known to have or that demonstrates advantageous properties when administered with a compound having the same mechanism of action as dextromethorphan. In one embodiment, such agents include those indicated as being useful in combination with dextromethorphan, including but not limited to, those described in U.S. Pat. Nos. 4,316,888; 4,446,140; 4,694,010; 4,898,860; 5,166,207; 5,336,980; 5,350,756; 5,366,980; 5,863,927; RE38,115; 6,197,830; 6,207,164; 6,583,152; and 7,114,547; as well as in US patent publications 2001/0044446; 2002/0103109; 2004/0087479; 2005/0129783; 2005/0203125; and 2007/0191411.

In one embodiment, the second therapeutic agent is an agent useful in the treatment or prevention of a disease or condition selected from, but not limited to, emotional lability; pseudobulbar affect; autism; neurological disorders and neurodegenerative diseases such as, e.g., dementia, amyotrophic lateral sclerosis (ALS, also known as Leu Gehrig's disease), Alzheimer's disease, Parkinson's disease, and multiple sclerosis; disturbances of consciousness disorders; brain injuries such as, e.g., stroke, traumatic brain injury, ischemic event, hypoxic event, and neuronal death; cardiovascular diseases such as, e.g., peripheral vascular diseases, myocardial infarctions, and atherosclerosis; glaucoma; tardive dyskinesia; diabetic neuropathy; retinopathic diseases; diseases or disorders caused by homocysteine-induced apoptosis; diseases or disorders caused by elevated levels of homocysteine; chronic pain; intractable pain; neuropathic pain; sympathetically mediated pain such as allodynia, hyperpathia, hyperalgesia, dysesthesia, paresthesia, deafferentation pain, and anesthesia dolorosa pain; pain associated with gastrointestinal dysfunction including, e.g., irritable bowel syndrome; mouth pain; epileptic seizures; tinnitus; sexual dysfunction; intractable coughing; dermatitis; addiction disorders such as, e.g., addiction to or dependence on stimulants, nicotine, morphine, heroine, other opiates, amphetamines, cocaine, and alcohol; RTT; voice disorders due to uncontrolled laryngeal muscle spasms including e.g., abductor spasmodic dysphonia, adductor spasmodic dysphonia, muscular tension dysphonia, and vocal tremor; methotrexate neurotoxicity; and fatigue caused by cancer.

In one embodiment, the second therapeutic agent is quinidine. Quinidine co-administration has at least two distinct beneficial effects. First, it greatly increases the quantity of dextromethorphan circulating in the blood. In addition, it also yields more consistent and predictable dextromethorphan concentrations. Research involving dextromethorphan or co-administration of quinidine and dextromethorphan, and the effects of quinidine on blood plasma concentrations, are described in the patent literature (see, e.g., U.S. Pat. Nos. 5,166,207, 5,863,927, 5,366,980, 5,206,248, 5,350,756 to Smith).

While quinidine is most commonly used for coadministration, other agents, such as but not limited to those described in Inaba et al., Drug Metabolism and Disposition. 1985; 13:443-447, Forme-Pfister et al., Biochem. Pharmacol. 1988; 37:3829-3835, and Broly et al., Biochem. Pharmacol. 1990; 39:1045-1053, can also be co-administered with dextromethorphan to reduce its metabolism. As reported in Inaba et al., CYP2D6 inhibitors with a $K_i$ value (Michaelis-Menton inhibition value) of 50 micromolar or lower include nortriptyline, chlorpromazine, domperidone, haloperidol, pipamperone, labetalol, metaprolol, oxprenolol, propranolol, timolol, mexiletine, quinine, diphenhydramine, ajmaline, lobeline, papaverine, and yohimbine. Compounds having particularly potent inhibitory activities include yohimbine, haloperidol, ajmaline, lobeline, and pipamperone, which have $K_i$ values ranging from 4 to 0.33 µM. In addition to the agents reported above, it has also been found that fluoxetine, sold by Eli Lilly and Co. under the trade name Prozac, is effective in increasing dextromethorphan concentrations in the blood of some people. In addition, any of the following compounds may be used to inhibit CYP2D6: terbinafine, cinacalcet, buprenorphine, imipramine, bupropion, ritonavir, sertraline, duloxetine, thioridazine, metoclopramide, paroxetine, or fluvoxamine. Dosages of other antioxidants will vary with the antioxidant, and are determined on an individual basis.

In one embodiment, the disclosure provides separate dosage forms of a compound of this disclosure and one or more of any of the above-described second therapeutic agents, wherein the dosage forms of the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously). In another embodiment, the compound of this disclosure and one or more of any of the above-described second therapeutic agents are provided in a single dosage form.

In the pharmaceutical compositions of the disclosure, the compound of the present disclosure is present in an effective amount. As used herein, the term "effective amount" refers to an amount which, when administered in a proper dosing regimen, is sufficient to reduce or ameliorate the severity, duration, or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this disclosure can range from 0.4 mg to 400 mg, from 4.0 mg to 350 mg, from 10 mg to 90 mg, or from 30 mg to 45 mg, inclusive. In some embodiments, an effective amount of a compound of this disclosure is about 45 mg, 34 mg, 30 mg, 28 mg, 24 mg, 23 mg, 20 mg, 18 mg, 15 mg, or 10 mg.

Effective doses will also vary, as recognized by those skilled in the art, depending on the diseases treated, the severity of the disease, the route of administration, the sex, age, and general health condition of the subject, excipient usage, the possibility of co-usage with other therapeutic treatments such as use of other agents and the judgment of the treating physician. In one embodiment, for example, guidance for selecting an effective dose can be determined by reference to the prescribing information for dextromethorphan.

The compounds of the present disclosure and the pharmaceutical compositions that comprise them demonstrate a longer clearance and produce a higher plasma exposure level 12 hours post-dosing as compared to a pharmaceutical composition comprising the same amount of dextromethorphan on a mole basis ("molar equivalent dextromethorphan composition"). Thus, in one embodiment, the disclosure provides a pharmaceutical composition comprising an effective amount of a compound of Formula I, the administration of which to a subject results in a plasma exposure level that is greater than the plasma exposure level of a molar equivalent dextromethorphan composition that is administered using the same dosing regimen.

In one embodiment, the plasma exposure level is at least 110%, 115%, 120% 125%, 130%, 135%, 140%, 145%, or more of the plasma exposure level of dextromethorphan produced by a molar equivalent dextromethorphan composition that is administered to an equivalent subject.

In one embodiment, the disclosure provides a pharmaceutical composition comprising 10-60 mg of a compound of Formula I, wherein the administration of the pharmaceutical composition to a subject results in a plasma exposure level in the range of 250-750 nanograms (ng)-hour (h)/mL (AUC).

In one embodiment, the disclosure provides a pharmaceutical composition comprising 10-60 mg of a compound of Formula I, wherein the administration of the pharmaceutical composition to a subject results in a plasma exposure level in the range of 400-1600 ng-h/mL (AUC).

In one embodiment, the disclosure provides a pharmaceutical composition comprising 10-60 mg of a compound of Formula I, wherein the administration of the pharmaceutical composition to a subject results in a plasma exposure level in the range of 500-1500 ng-h/mL (AUC).

In one embodiment, the disclosure provides a pharmaceutical composition comprising 10-60 mg of a compound of Formula I, wherein the administration of the pharmaceutical composition to a subject results in a plasma exposure level in the range of 1000-1500 ng-h/mL (AUC).

In one embodiment, the disclosure provides a pharmaceutical composition comprising an effective amount of a compound of Formula I, the administration of which to a subject results in a decrease in rate and amount of metabolite production as compared to a molar equivalent dextromethorphan composition that is administered using the same dosing regimen.

In one embodiment, the disclosure provides a pharmaceutical composition comprising 10-60 mg of a compound of Formula I, the administration of which to a subject results in a plasma exposure level of deuterated dextrorphan isotopologues less than or equal to 1000 ng-h/mL.

In one embodiment, the disclosure provides a pharmaceutical composition comprising 10-60 mg of a compound of Formula I, the administration of which to a subject results in a plasma exposure level of deuterated dextrorphan isotopologues less than or equal to 750 ng-h/mL.

In one embodiment, the disclosure provides a pharmaceutical composition comprising 10-60 mg of a compound of Formula I, the administration of which to a subject results in a plasma exposure level of deuterated dextrorphan isotopologues less than or equal to 500 ng-h/mL.

In one embodiment, the disclosure provides a pharmaceutical composition comprising an effective amount of a compound of Formula I, the administration of which to a subject results in both an increase in the plasma exposure level of a compound of Formula I and a decrease in the plasma exposure level of dextromethorphan metabolite isotopologues, particularly deuterated dextrorphan isotopologues, as compared to the plasma exposure levels of dextromethorphan and dextrorphan produced from a molar equivalent dextromethorphan composition that is administered in the same dosing regimen.

In one embodiment, the disclosure provides a pharmaceutical composition comprising 10-60 mg of a compound of Formula I, said composition providing a plasma exposure level of a compound of Formula I of from about 1750 to about 250 ng-h/mL after repeated administration to a subject every 12 hours through steady-state conditions.

In one embodiment, for pharmaceutical compositions that comprise a second therapeutic agent, an effective amount of the second therapeutic agent is between about 0.01% to 100% of the dosage normally utilized in a monotherapy regime using just that agent. The normal monotherapeutic dosages of these second therapeutic agents are well known in the art. See, e.g., Wells et al., eds., Pharmacotherapy Handbook, 2nd Edition, Appleton and Lange, Stamford, CT (2000); PDR Pharmacopoeia, Tarascon Pocket Pharmacopoeia 2000, Deluxe Edition, Tarascon Publishing, Lorna Linda, CA. (2000), each of which are incorporated herein by reference in their entirety.

In one embodiment, it is expected that some of the second therapeutic agents referenced above will act synergistically with the compounds of this disclosure. When this occurs, it will allow the effective dosage of the second therapeutic agent and/or the compound of this disclosure to be reduced from that required in a monotherapy. This has the advantage of minimizing toxic side effects of either the second therapeutic agent of a compound of this disclosure, synergistic improvements in efficacy, improved ease of administration or use and/or reduced overall expense of compound preparation or formulation.

Thus, in one embodiment, the disclosure provides a pharmaceutical composition comprising 10-60 mg of a compound of Formula I and 2.5-30 mg quinidine, said composition providing a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

In one embodiment, the disclosure provides a pharmaceutical composition comprising 10-60 mg of a compound of Formula I and 2.5-20 mg quinidine, said composition providing a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without quinidine.

In one embodiment, the disclosure provides a pharmaceutical composition comprising 10-60 mg of a compound of Formula I and 2.5-10 mg quinidine, said composition providing a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

In one embodiment, the disclosure provides a pharmaceutical composition comprising a 15-45 mg of a compound of Formula I and 2.5-30 mg quinidine, said composition providing a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

In one embodiment, the disclosure provides a pharmaceutical composition comprising a 20-35 mg of a compound of Formula I and 2.5-30 mg quinidine, said composition providing a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

In one embodiment, the disclosure provides a pharmaceutical composition comprising a compound of Formula I and quinidine, said composition providing lower urine concentrations of a compound of Formula I and higher urine concentrations of deuterated dextrorphan isotopologues in a subject as compared to urine concentrations of dextromethorphan and dextrorphan in an equivalent subject resulting from the administration of a molar equivalent dextromethorphan composition additionally comprising the same amount of quinidine and administered according to the same dosing regimen.

In one embodiment, a compound of Formula I and quinidine are administered in a combined dose, or in separate doses. The separate doses may be administered substantially simultaneously. In one embodiment, the weight ratio of the compound of Formula I to quinidine is about 1:1 or less. In some embodiments, the weight ratio is about 1:1, 1:0.95, 1:0.9, 1:0.85, 1:0.8, 1:0.75, 1:0.7, 1:0.65, 1:0.6, 1:0.55 or 1:0.5 or less. Likewise, in certain embodiments, dosages have a weight ratio of the compound of Formula I to quinidine less than about 1:0.5, for example, about 1:0.45, 1:0.4, 1:0.35, 1:0.3, 1:0.25, 1:0.2, 1:0.15, or 1:0.1, 1:0.09, 1:0.08, 1:0.07, 1:0.06, 1:0.05, 1:0.04, 1:0.03, 1:0.02, or 1:0.01, or less. The weight ratios can be for example, about 1:0.75, about 1:0.68, about 1:0.6, about 1:0.56, about 1:0.5, about 1:0.44, about 1:0.39, about 1:0.38, about 1:0.31, about 1:0.30, about 1:0.29, about 1:0.28, about 1:0.27, about 1:0.26, about 1:0.25, about 1:0.24, about 1:0.23, about 1:0.22, about 1:0.21, about 1:0.20, about 1:0.19, about 1:0.18, about 1:0.17, 1:0.16, about 1:0.15, about 1:0.14, about 1:0.13, about 1:0.12, about 1:0.11 and about 1:0.10. In some embodiments, the weight ratios for free base of a compound of Formula I to free base of quinidine is about 1:0.68, about 1:0.56, about 1: 0.44, about 1:0.38. In other embodiments, the weight ratios for free base of a compound of Formula I to free base of quinidine is about 1: 0.30, about 1:0.22, about 1: 0.19, about 1: 0.18, about 1: 0.16, and about 1:0.15.

In certain embodiments, when a compound of Formula I and quinidine are administered at a weight ratio of 1:1 or less, less than 50 mg quinidine is administered at any one time. For example, in certain embodiments, quinidine is administered at about 30, 25, or 20 mg or less. In other embodiments, quinidine is administered at about 15, 10, 9.5, 9.0, 8.5, 8.0, 7.5, 7.0, 6.5, 6.0, 5.5, 5.0, or less. In other embodiments, quinidine is administered at about 5.00, 4.95, 4.90, 4.85, 4.80, 4.75, 4.70, 4.65, 4.60, 4.55, 4.50, 4.45, 4.40, 4.35, 4.30, 4.25, 4.20, 4.15, 4.10, 4.05, 4.00, 3.95, 3.90, 3.85, 3.80, 3.75, 3.70, 3.65, 3.60, 3.55, 3.50, 3.45, 3.40, 3.35, 3.30, 3.25, 3.20, 3.15, 3.10, 3.05, 3.00, 2.95, 2.90, 2.85, 2.80, 2.75, 2.70, 2.65, 2.60, 2.55, 2.50, 2.45, 2.40, 2.35, 2.30, 2.25, 2.20, 2.15, 2.10, 2.05, 2.00, 1.95, 1.90, 1.85, 1.80, 1.75, 1.70, 1.65, 1.60, 1.55, 1.50, 1.45, 1.40, 1.35, 1.30, 1.25, 1.20, 1.15, 1.10, 1.05, 1.00, 0.95, 0.90, 0.85, 0.80, 0.75, 0.70, 0.65, 0.60, 0.55, 0.50, 0.45, 0.40, 0.35, 0.30, 0.25, 0.20, 0.15, 0.10, or 0.05, or less.

In some embodiments, the combined dose (or separate doses simultaneously administered) at a weight ratio of 1:1 or less is administered once daily, twice daily, three times daily, four times daily, or more frequently so as to provide the subject with a certain dosage level per day, for example: 60 mg quinidine and 60 mg of a compound of Formula I per day provided in two doses, each dose containing 30 mg quinidine and 30 mg of a compound of Formula I; 50 mg quinidine and 50 mg of a compound of Formula I per day provided in two doses, each dose containing 25 mg quinidine and 25 mg of a compound of Formula I; 40 mg quinidine and 40 mg of a compound of Formula I per day provided in two doses, each dose containing 20 mg quinidine and 20 mg of a compound of Formula I; 30 mg quinidine and 30 mg of a compound of Formula I per day provided in two doses, each dose containing 15 mg quinidine and 15 mg of a compound of Formula I; or 20 mg quinidine and 20 mg of a compound of Formula I per day provided in two doses, each dose containing 10 mg quinidine (i.e., about 9 mg of quinidine free base) and 10 mg of a compound of Formula I. In some embodiments, the total amount of a compound of Formula I and quinidine in a combined dose may be adjusted, depending upon the number of doses to be administered per day, so as to provide a suitable daily total dosage to the subject, while maintaining a weight ratio of 1:1 or less.

In some embodiments, the daily dose of a compound of Formula I and quinidine is 30 mg of a compound of Formula IV and 30 mg quinidine sulfate. Other dosages include, for example, 15 mg of a compound of Formula IV and 9 mg quinidine sulfate (corresponding to approximately 11 mg of a compound of Formula I and approximately 7.5 mg quinidine); 23 mg of a compound of Formula IV and 9 quinidine sulfate (corresponding to approximately 17 mg of a compound of Formula I and approximately 7.5 mg quinidine); 20 mg of a compound of Formula IV and 10 quinidine sulfate (corresponding to approximately 15 mg of a compound of Formula I and 8.3 mg quinidine); 30 mg of a compound of Formula IV and 10 quinidine sulfate (corresponding to approximately 22 mg of a compound of Formula I and 8.3 mg quinidine).

A dose of 30 mg of a compound of Formula IV (of molecular formula $C_{18}H_{19}D_6NO \cdot HBr \cdot H_2O$) and 30 mg quinidine sulfate (of molecular formula $(C_{20}H_{24}N_2O_2)_2 \cdot H_2SO_4 \cdot 2H_2O$) may be administered or used (corresponding to approximately 22.22 mg of a compound of Formula I and 25 mg quinidine). Other dosages for a compound of Formula I or Formula IV include, for example, 24 mg of a compound of Formula IV and 4.75 mg quinidine sulfate (corresponding to approximately 18 mg of a compound of Formula I and approximately 3.96 mg quinidine); 34 mg of a compound of Formula IV and 4.75 quinidine sulfate (corresponding to approximately 25.18 mg of a compound of Formula I and approximately 3.96 mg quinidine); 18 mg of a compound of Formula IV and 4.9 quinidine sulfate (corresponding to approximately 13.33 mg of a compound of Formula I and 4.08 mg quinidine); 24 mg of a compound of Formula IV and 4.9 quinidine sulfate (corresponding to approximately 17.78 mg of a compound of Formula I and 4.08 mg quinidine); 28 mg of a compound of Formula IV and 4.9 quinidine sulfate (corresponding to approximately 20.74 mg of a compound of Formula I and 4.08 mg quinidine); 30 mg of a compound of Formula IV and 4.9 quinidine sulfate (corresponding to approximately 22.22 mg of a compound of Formula I and 4.08 mg quinidine); 34 mg of a compound of Formula IV and 4.9 quinidine sulfate (corresponding to approximately 25.18 mg of a compound of Formula I and 4.08 mg quinidine).

In some embodiments, the therapy is initiated at a lower daily dose, for example about 18 or 30 mg of a compound of Formula I in combination with about 2.5 to 10 mg quinidine per day, and increased up to about 90 mg of a compound of Formula I in combination with about 10 to 20 mg quinidine, or higher, depending on the subject's global response. In some embodiments, infants, children, subjects over 65 years, and those with impaired renal or hepatic function, initially receive low doses, that may be titrated based on individual response(s) and blood level(s). Generally, a daily dosage of 18 to 90 mg of a compound of Formula I and 4.75 to 20 mg quinidine is well-tolerated by most subjects.

As will be apparent to those skilled in the art, dosages outside of these disclosed ranges may be administered in some cases. Further, it is noted that the ordinary skilled clinician or treating physician will know how and when to interrupt, adjust, or terminate therapy in consideration of individual response.

Methods of Treatment

In one embodiment, the disclosure provides a method of modulating the activity of the $\sigma_2$ receptor, N-methyl-D-aspartate (NDMA), or the activity of the α3β4 nicotinic receptor in a cell, comprising contacting a cell with one or more compounds of Formula I.

In one embodiment, the disclosure provides a method of inhibiting neurotransmitters, such as glutamate, from activating receptors in the brain and/or inhibiting the uptake of dopamine and serotonin by administering a compound of Formula I.

In one embodiment, the disclosure provides a method of treating a subject suffering from, or susceptible to, a disease that is beneficially treated by dextromethorphan comprising the step of administering to said subject an effective amount of a compound of Formula I or a composition comprising such a compound. Such diseases are well known in the art and are disclosed in, but are not limited to, those described in U.S. Pat. Nos. 4,316,888; 4,446,140; 4,694,010; 4,898,860; 5,166,207; 5,336,980; 5,350,756; 5,366,980; 5,863,927; RE38,115; 6,197,830; 6,207,164; 6,583,152; and 7,114,547; as well as in US patent publications 2001/0044446; 2002/0103109; 2004/0087479; 2005/0129783; 2005/0203125; and 2007/0191411.

In one embodiment, such diseases include, but are not limited to, emotional lability; pseudobulbar affect; autism; neurological disorders and neurodegenerative diseases such as, e.g., dementia, amyotrophic lateral sclerosis (ALS, also known as Leu Gehrig's disease), Alzheimer's disease, Parkinson's, and multiple sclerosis; disturbances of consciousness disorders; brain injuries such as, e.g., stroke, traumatic brain injury, ischemic event, hypoxic event and neuronal death; cardiovascular diseases such as, e.g., peripheral vascular diseases, strokes, myocardial infarctions, and atherosclerosis; glaucoma; tardive dyskinesia; diabetic neuropathy; retinopathic diseases; diseases or disorders caused by homocysteine-induced apoptosis; diseases or disorders caused by elevated levels of homocysteine; chronic pain;

intractable pain; neuropathic pain; sympathetically mediated pain such as allodynia, hyperpathia, hyperalgesia, dysesthesia, paresthesia, deafferentation pain, and anesthesia dolorosa pain; pain associated with gastrointestinal dysfunction including, e.g., irritable bowel syndrome; mouth pain; epileptic seizures; tinnitus; sexual dysfunction; intractable coughing; dermatitis; addiction disorders such as, e.g., addiction to or dependence on stimulants, nicotine, morphine, heroine, other opiates, amphetamines, cocaine, and 15 alcohol; RTT; voice disorders due to uncontrolled laryngeal muscle spasms including, e.g., abductor spasmodic dysphonia, adductor spasmodic dysphonia, muscular tension dysphonia, and vocal tremor; methotrexate neurotoxicity; and fatigue caused by cancer.

In one embodiment, methods of treatment delineated herein also include those wherein the subject is identified as in need of a particular stated treatment. Identifying a subject in need of such treatment can be in the judgment of a subject or a health care professional, and can be subjective (e.g. opinion) or objective (e.g. measurable by a test or diagnostic method).

In the methods of treatment delineated herein, a pharmaceutical composition comprising an effective amount of a compound of Formula I is administered to a subject, resulting in a plasma exposure level that is greater than the plasma exposure level of a molar equivalent dextromethorphan composition that is administered using the same dosing regimen. The plasma exposure level is at least 110%, 115%, 120% 125%, 130%, 135%, 140%, 145%, or more of the plasma exposure level of dextromethorphan produced by a molar equivalent dextromethorphan composition that is administered to an equivalent subject.

In one embodiment, the disclosure provides a method for treating a disease in a subject in need of such treatment, said method comprising administering to the subject a pharmaceutical composition comprising 10-60 mg of a compound of Formula I, wherein the administration of the pharmaceutical composition to the subject results in a plasma exposure level in the range of 250-750 nanograms (ng)-hour (h)/mL (AUC).

In one embodiment, the disclosure provides a method for treating a disease in a subject in need of such treatment, said method comprising administering to the subject a pharmaceutical composition comprising 10-60 mg of a compound of Formula I, wherein the administration of the pharmaceutical composition to the subject results in a plasma exposure level in the range of 400-1600 ng-h/mL (AUC).

In one embodiment, the disclosure provides a method for treating a disease in a subject in need of such treatment, said method comprising administering to the subject a pharmaceutical composition comprising 10-60 mg of a compound of Formula I, wherein the administration of the pharmaceutical composition to the subject results in a plasma exposure level in the range of 500-1500 ng-h/mL (AUC).

In one embodiment, the disclosure provides a method for treating a disease in a subject in need of such treatment, said method comprising administering to the subject a pharmaceutical composition comprising 10-60 mg of a compound of Formula I, wherein the administration of the pharmaceutical composition to the subject results in a plasma exposure level in the range of 1000-1500 ng-h/m L (AUC).

In one embodiment, the disclosure provides a method for treating a disease in a subject in need of such treatment, said method comprising administering to the subject a pharmaceutical composition comprising an amount of a compound of Formula I, effective to decrease in rate and amount of metabolite production as compared to a molar equivalent dextromethorphan composition that is administered using the same dosing regimen.

In one embodiment, the disclosure provides a method for treating a disease in a subject in need of such treatment, said method comprising administering to the subject a pharmaceutical composition comprising 10-60 mg of a compound of Formula I, the administration of which to a subject results in a plasma exposure level of deuterated dextrorphan isotopologues less than or equal to 1000 ng-h/mL.

In one embodiment, the disclosure provides a method for treating a disease in a subject in need of such treatment, said method comprising administering to the subject a pharmaceutical composition comprising 10-60 mg of a compound of Formula I, the administration of which to a subject results in a plasma exposure level of deuterated dextrorphan isotopologues less than or equal to 750 ng-h/mL.

In one embodiment, the disclosure provides a method for treating a disease in a subject in need of such treatment, said method comprising administering to the subject a pharmaceutical composition comprising 10-60 mg of a compound of Formula I, the administration of which to a subject results in a plasma exposure level of deuterated dextrorphan isotopologues less than or equal to 500 ng-h/mL.

In one embodiment, the disclosure provides a method for treating a disease in a subject in need of such treatment, said method comprising administering to the subject a pharmaceutical composition comprising 10-60 mg of a compound of Formula I, the administration of which to a subject results in both an increase in the plasma exposure level of a compound of Formula I, and a decrease in the plasma exposure level of dextromethorphan metabolite isotopologues, particularly deuterated dextrorphan isotopologues, as compared to the plasma exposure levels of dextromethorphan and dextrorphan produced from a molar equivalent dextromethorphan composition that is administered in the same dosing regimen.

In one embodiment, the disclosure provides a method for treating a disease in a subject in need of such treatment, said method comprising administering to the subject a pharmaceutical composition comprising 10-60 mg of a compound of Formula I, said composition providing a plasma exposure level of a compound of Formula I of from about 1750 to about 250 ng-h/m L after repeated administration to a subject every 12 hours through steady-state conditions.

In one embodiment, any of the above methods of treatment comprises the further step of co-administering to the subject one or more second therapeutic agents. The choice of second therapeutic agent may be made from any second therapeutic agent known to be useful for co-administration with dextromethorphan. The choice of second therapeutic agent is also dependent upon the particular disease or condition to be treated. Examples of second therapeutic agents that may be employed in the methods of this disclosure are those set forth above for use in combination compositions comprising a compound of this disclosure and a second therapeutic agent.

In one embodiment, the combination therapies of this disclosure include co-administering to a subject in need thereof a compound of Formula I, or a composition comprising such compound, and quinidine sulfate.

The term "co-administered" as used herein means that the second therapeutic agent may be administered together with a compound of this disclosure as part of a single dosage form (such as a composition of this disclosure comprising a compound of the disclosure and a second therapeutic agent as described above) or as separate, multiple dosage forms. In one embodiment, the additional agent may be administered prior to, consecutively with, or following the administration of a compound of this disclosure. In such combination therapy treatment, both the compounds of this disclosure and the second therapeutic agent(s) are administered by conventional methods. The administration of a composition of this disclosure, comprising both a compound of the disclosure and a second therapeutic agent, to a subject does not preclude the separate administration of that same therapeutic agent, any other second therapeutic agent, or any compound of this disclosure to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, CT. (2000); PDR Pharmacopoeia, Tarascon Pocket Pharmacopoeia 2000, Deluxe Edition, Tarascon Publishing, Lorna Linda, CA. (2000), and other medical texts. However, it is well within the skilled artisan's purview to determine the second therapeutic agent's optimal effective-amount range.

In one embodiment of the disclosure, where a second therapeutic agent is administered to a subject, the effective amount of the compound of this disclosure is less than its effective amount would be where the second therapeutic agent is not administered. In another embodiment, the effective amount of the second therapeutic agent is less than its effective amount would be where the compound of this disclosure is not administered. In this way, undesired side effects associated with high doses of either agent may be minimized. Other potential advantages (including without limitation improved dosing regimens and/or reduced drug cost) will be apparent to those of skill in the art.

In one embodiment, the disclosure provides the use of a compound of Formula I alone or together with one or more of the above-described second therapeutic agents in the manufacture of a medicament, either as a single composition or as separate dosage forms, for treatment or prevention in a subject of a disease, disorder, or symptom set forth above. In one embodiment, the disclosure provides the use of a compound of Formula I for the treatment or prevention in a subject of a disease, disorder, or symptom thereof delineated herein.

Thus, in one embodiment, the disclosure provides a method of treating a disease in a subject in need of such treatment, the method comprising co-administering 10-60 mg of a compound of Formula I and 2.5-30 mg quinidine, so that the composition provides a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

Thus, in one embodiment, the disclosure provides a method of treating a disease in a subject in need of such treatment, the method comprising co-administering 10-60 mg of a compound of Formula I and 2.5-20 mg quinidine, so that the composition provides a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

Thus, in one embodiment, the disclosure provides a method of treating a disease in a subject in need of such treatment, the method comprising co-administering 10-60 mg of a compound of Formula I and 2.5-10 mg quinidine, so that the composition provides a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

Thus, in one embodiment, the disclosure provides a method of treating a disease in a subject in need of such treatment, the method comprising co-administering 15-45 mg of a compound of Formula I and 2.5-30 mg quinidine, so that the composition provides a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

Thus, in one embodiment, the disclosure provides a method of treating a disease in a subject in need of such treatment, the method comprising co-administering 20-35 mg of a compound of Formula I and 2.5-30 mg quinidine, so that the composition provides a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

Thus, in one embodiment, the disclosure provides a method of treating a disease in a subject in need of such treatment, the method comprising co-administering a compound of Formula I and quinidine, so that the composition provides lower urine concentrations of a compound of Formula I and higher urine concentrations of deuterated dextrorphan isotopologues in a subject as compared to urine concentrations of dextromethorphan and dextrorphan in an equivalent subject resulting from the administration of a molar equivalent dextromethorphan composition additionally comprising the same amount of quinidine and administered according to the same dosing regimen.

The present disclosure may be further understood by reference to the following examples. Those having ordinary skill in the art and access to the teachings provided herein will recognize additional modifications, applications, embodiments, and substitution of equivalents that fall within the scope of the disclosure. The following examples are intended for illustration purposes only and should not be construed as limiting the scope of the disclosure in any way. Further, the section headings used herein are for organizational purposes only and are not to be construed as limiting the subject matter described.

Example 1

Synthesis of compounds of Formula (I). Each of the reactions and numbered intermediates described below refer to the corresponding reactions and intermediates in Scheme 1, supra.

Reaction (i) (Intermediate d6-DM-J Hydrochloride): A solution of detromethorphan hydrobromide (1.1 kg, 2.97 mol, 1.0 eq) in toluene (13.2 L, 12 v) was mixed with aqueous sodium hydroxide (1 M concentration). After stirring, the organic phase was separated, washed with water to neutral pH, and azeotropically dried. 1-Chloroethyl chloroformate (0.552 kg, 3.86 mol, 1.3 eq) was added to the solution and the mixture was stirred until the conversion was ≥93%. The mixture was heated to 65~70° C. and methanol (2.09 kg, 1.9 kg/kg) was slowly introduced. Heating was continued until the reaction conversion was ≥98%. The reaction mixture was cooled and concentrated under vacuum until the methanol level was reduced to NMT 100 ppm. Toluene (4.0 L, 3.6 v) was added and the mixture was again concentrated under vacuum. This procedure was continued until the residual methanol level was about 100 ppm or less. Isopropanol was added and the mixture was heated and cooled. The level of impurity d6-DM-JA and dextromethorphan were determined by HPLC (target level was NMT 0.5% for d6-DM-JA and NMT 2.0% for dextromethorphan). The solid d6-DM-J HCl was isolated by filtration and rinsed with portions of toluene. d6-DM-J HCl was dried at about 40° C. until the toluene level was ≤1%. Compound d6-DM-J HCl was obtained in 84.2% yield with a purity of 98.2%. $^1$HNMR (CDCl$_3$, 500 MHz): δ9.67 (2H, s), 7.09 (1H, d, J=5 Hz), 6.81 (1H, d, J=5 Hz), 6.76 (1H, dd, J=2.5 Hz, 1 Hz), 3.77 (3H, s), 3.70 (1H, s), 3.14~3.27 (3H, m), 2.78~2.67 (1H, m), 2.34 (1H, d, J=15 Hz), 2.17 (1H, d, J=10 Hz), 2.00 (1H, dt, J=10 Hz, 15 Hz), 1.63 (1H, d, J=15 Hz), 1.57-1.33 (5H, m), 1.33~1.20 (1H, m), 1.12~0.97 (1H, m).

Reaction (ii) (Intermediate d6-DM-F): d6-DM-J hydrochloride (500 g, 1.702 mol, 1.0 eq) was dissolved in tetrahydrofuran and cooled to −80~−70° C. 2.5M n-Butyllithium (1174.5 g, 2.5 eq) was added followed by iodomethane-D3 (271.3 g, 1.872 mol, 1.1eq). Reaction completion was monitored and additional portions of iodomethane-D3 (29.6 g, 0.204 mol, 0.12 eq) were added until d6-DM-J was consumed. Aqueous ammonium chloride (3000 g, 6.0 g/g, 20% concentration) was added and the mixture was warmed under reduced pressure to remove any remaining iodomethane-D3. Purified water (1 L, 2 v) was added, the organic phase was separated, and the aqueous phase was extracted with methyl-t-butyl ether. The combined organic phase was concentrated under vacuum and the solvent was exchanged to methanol (1 L, 2 v). Purified water (3.5 L, 7 v) was slowly added and the mixture was cooled. The d6-DM-F was isolated by filtration, washed with purified water, and dried to give a compound of Formula (III). d6-DM-F was recrystallized from methanol/water. The yield obtained was 84.5% with a purity of 98.9%. HNMR (CDCl$_3$, 500 MHz): δ7.05 (1H, d, J=10 Hz), 6.81 (1H, d, J=5 Hz), 6.71 (1H, dd, J=5 Hz, 10 Hz), 3.77 (3H, s), 3.03~2.95 (2H, m), 2.75 (1H, dd, J=5 Hz, 1.5 Hz), 2.63 (1H, dd, J=5 Hz, 10 Hz), 2.35 (1H, d, J=15 Hz), 2.23 (1H, dt, J=10 Hz, 15 Hz), 2.02 (1H, d, J=15 Hz), 1.91 (1H, dt, J=15 Hz, 15 Hz), 1.64 (1H, d, J=15 Hz), 1.53 (1H, d, J=15 Hz), 1.47~1.22 (5H, m), 1.17~1.05 (1H, m).

Reaction (iii) (Intermediate d6-DM-H): d6-DM-F (2576 g, wt=83.0%, 7.791 mol, 1.0 eq) was mixed with hydrobromic acid (9608 g, 3.73 g/g) and heated to 90~95° C. until the d6-DM-F level was ≤1%. The cool mixture was mixed with aqueous potassium carbonate (20% concentration) and 2-methyltetrahydrofuran (38.6 L, 15 v) was added. The organic phase was separated and washed with purified water. The combined aqueous phase was extracted with 2-methyl tetrahydrofuran. The combined organic phase was concentrated under vacuum and the solvent was exchanged to n-heptane. The mixture was cooled, filtered, washed with n-heptane, and dried. Compound d6-DM-H was obtained in 78.8% yield and with a purity of 99.0%. HNMR (CDCl$_3$, 500 MHz): δ6.92 (1H, d, J=5 Hz), 6.71 (1H, d, J=2.5 Hz), 6.58 (1H, dd, J=5 Hz, 10 Hz), 2.94 (1H, d, J=20 Hz), 2.80-2.75 (1H, m), 2.60 (1H, dd, J=5 Hz, 15 Hz), 2.45-2.30 (2H, m), 2.11 (1H, dt, J=15 Hz, 15 Hz), 1.78 (1H, d, J=10 Hz), 1.72~1.50 (2H, m), 1.50 (1H, br s), 1.42~1.10 (6H, m).

Reaction (iv) (Intermediate d6-DM Free Base): d6-DM-H (748.7 g, wt=93.5%, 2.6883 mol, 1.0 eq) was mixed with dimethylformamide (8.12 L, 11.6 v) and the resulting solution tested for water content. If the water content was >0.05%, molecular sieve powder (4 A) was added and was removed after stirring by filtration. Potassium t-butoxide (362.0 g, 3.226 mol, 1.2 eq) was added to the solution and after stirring, a solution of iodomethane-D3 (448.1 g, 3.092 mol, 1.15 eq) in dimethylformamide was added. The reaction was continued until ≤5% d6-DM-H remained. Purified water was added and d6-DM Free Base was isolated by filtration. The filter cake was washed with water and dried to give a compound of Formula (I). A compound of Formula (I) was obtained in 78.9% yield with a purity of 99.3%. HNMR (CDCl$_3$, 500 MHz): δ7.02 (1H, d, J=10 Hz), 6.79 (1H, d, J=5 Hz), 6.68 (1H, dd, J=5 Hz, 10 Hz), 2.96 (1H, d, J=20 Hz), 2.82~2.75 (1H, m), 2.58 (1H, dd, J=5 Hz, 20 Hz), 2.42 (1H, dd, J=5 Hz, 10 Hz), 2.35 (1H, d, J=10 Hz), 2.07 (1H, dt, J=15 Hz, 15 Hz), 1.81 (1H, d, J=10 Hz), 1.76 (1H, dt, J=15 Hz, 15 Hz), 1.64 (1H, d, J=10 Hz), 1.51 (1H, d, J=10 Hz), 1.45~1.07 (6H, m).

Example 2

Synthesis of a compound of Formula (IV). Each of the reactions and numbered intermediates described below refer to the corresponding reactions and intermediates in Scheme 3, supra.

Reaction (v) (d6-DM Hydrobromide Monohydrate): All solutions were filtered using a 0.45 μm filter and all operations are carried out in a Class 100,000 clean room. Purified water (1.1 L, 4 v) and d6-DM Free Base (277.4 g, 1.00 mol) were mixed in a reactor. A hydrobromic acid solution (48% concentration, 177.0 g, 1.05 mol) was added, followed by purified water (0.28 L, 1 v). The resulting mixture was heated to 65~70° C. until a solution forms and then was cooled to allow crystallization to occur. The mixture was heated and cooled through several cycles to optimize particle size and then was cooled to ambient temperature. The product was isolated by filtration, washed with purified water, and dried at 40-45° C. to give a compound of Formula (IV). The compound of Formula (IV) was obtained in 85.0% yield with a purity of 99.6%. HNMR (CDCl$_3$, 500 MHz): δ7.07 (1H, d, J=10 Hz), 6.79 (1H, d, J=3.5 Hz), 6.68 (1H, d, J=10 Hz), 3.51 (1H, m), 3.17~29.0 (3H, m), 2.70~2.20 (4H, m), 1.63 (1H, d, J=20 Hz), 1.60~1.35 (5H, m), 1.30~1.15 (1H, m), 2.07 (1H, dq, J=15 Hz, 30 Hz).

What is claimed is:

1. A method for synthesizing a deuterated dextromethorphan of Formula (I)

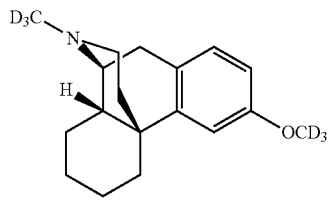

(I)

the method comprising:
(i) O-demethylating the methoxy group of a dextromethorphan compound of Formula (II)

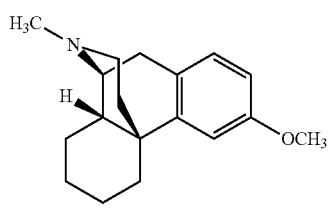

(II)

to a compound of Formula (VIII)

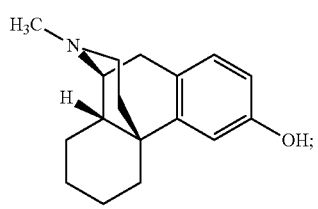

(VIII)

isolating the compound of Formula (VIII);
(ii) deuterating the O-demethylated compound of Formula (VIII) to a compound of Formula (VII)

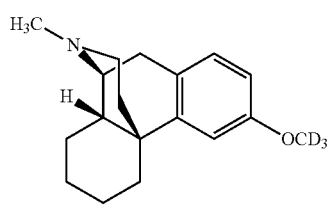

(VII)

by O-methylation in the presence of a base and iodomethane-$D_3$ at temperatures in the range of −10° C. to 10° C. inclusive;
(iii) N-demethylating the tertiary amine of a dextromethorphan compound of Formula (VII) to a compound of Formula (IX);

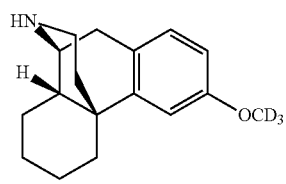

(IX)

isolating the compound of Formula (IX); and
(iv) deuterating the N-demethylated compound of Formula (IX) to the compound of Formula (I) by N-methylation in the presence of a base and iodomethane-$D_3$ at a temperature in the range of −90° C. to 90° C. inclusive.

2. The method of claim 1, wherein the N-demethylation of step (iii) is conducted in the presence of 1-chloroethyl chloroformate.

3. The method of claim 1, wherein the O-demethylation of step (i) is conducted in the presence of hydrobromic acid.

4. The method of claim 1, wherein the base used in step (iv) is chosen from sodium carbonate, cesium carbonate, potassium carbonate, sodium bicarbonate, potassium bicarbonate, sodium hydroxide, potassium hydroxide, potassium tert-butoxide, sodium hydride, n-butyllithium, lithium diisopropylamide, and a tertiary organic amine.

5. The method of claim 1, wherein the base used in step (ii) is chosen from potassium carbonate, sodium hydride, sodium methoxide, and potassium t-butoxide.

6. The method of claim 1, further comprising converting the compound of Formula (I) to a hydrobromide monohydrate salt of Formula (IV)

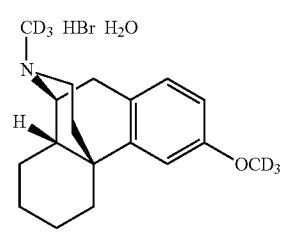

(IV)

by crystallization using a solution comprising hydrobromic acid.

* * * * *